(12) United States Patent
Mikhail et al.

(10) Patent No.: US 9,084,643 B2
(45) Date of Patent: Jul. 21, 2015

(54) ONE WAY SLIDING DEVICE FOR INTRAMEDULLARY INTERTROCHANTERIC FIXATION IMPLANTS

(75) Inventors: George A. Mikhail, Chester Springs, PA (US); Mark Siravo, Norristown, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 463 days.

(21) Appl. No.: 13/122,887

(22) PCT Filed: Sep. 23, 2009

(86) PCT No.: PCT/US2009/058019
§ 371 (c)(1),
(2), (4) Date: Apr. 6, 2011

(87) PCT Pub. No.: WO2010/053628
PCT Pub. Date: May 14, 2010

(65) Prior Publication Data
US 2011/0196370 A1    Aug. 11, 2011

Related U.S. Application Data

(60) Provisional application No. 61/111,825, filed on Nov. 6, 2008.

(51) Int. Cl.
*A61B 17/74* (2006.01)
(52) U.S. Cl.
CPC .................. *A61B 17/744* (2013.01)

(58) Field of Classification Search
USPC ...................................... 606/62–68
See application file for complete search history.

(56) References Cited

U.S. PATENT DOCUMENTS

| 6,406,477 | B1* | 6/2002 | Fujiwara .................. 606/67 |
| 6,648,889 | B2* | 11/2003 | Bramlet et al. ........... 606/62 |
| 6,685,706 | B2 | 2/2004 | Padget et al. |
| 6,887,243 | B2 | 5/2005 | Culbert |
| 6,890,333 | B2 | 5/2005 | von Hoffmann et al. |

(Continued)

FOREIGN PATENT DOCUMENTS

| CN | 2516116 | 10/2002 |
| EP | 1547534 | 6/2005 |

(Continued)

*Primary Examiner* — Jerry Cumberledge
(74) *Attorney, Agent, or Firm* — Fay Kaplun & Marcin, LLP

(57) ABSTRACT

A device for treating fractures, comprises an intramedullary member sized and shaped for insertion along a longitudinal axis of a bone within a medullary canal thereof, the intramedullary member including an opening extending obliquely therethrough, the opening, when the intramedullary member is in a desired position within a bone, aligning with a desired axis along which an implant is to be inserted into a bone, the intramedullary member including a channel formed therewithin and opening to the opening and a locking mechanism mounted in the channel, the locking mechanism including a locking abutting structure extending into the opening in combination with an implant sized to be slidably received through the opening and inserted along the desired axis, the implant including a plurality of implant abutting structures aligned to engage the locking abutting structure preventing medial movement of the implant relative to the intramedullary member.

18 Claims, 22 Drawing Sheets

(56) References Cited

U.S. PATENT DOCUMENTS

| | | |
|---|---|---|
| 6,942,668 B2 | 9/2005 | Padget et al. |
| 8,092,454 B2 * | 1/2012 | Sohngen .................... 606/67 |
| 2002/0032445 A1 | 3/2002 | Fujiwara |
| 2002/0133156 A1 * | 9/2002 | Cole ........................ 606/62 |
| 2005/0069397 A1 * | 3/2005 | Shavit et al. ............... 411/457 |
| 2005/0143739 A1 * | 6/2005 | Shinjo et al. ................ 606/62 |
| 2005/0203510 A1 * | 9/2005 | Sohngen .................... 606/60 |
| 2006/0009767 A1 * | 1/2006 | Kiester ...................... 606/61 |
| 2007/0049938 A1 | 3/2007 | Wallace et al. |
| 2007/0049939 A1 | 3/2007 | Wallace et al. |
| 2007/0049940 A1 | 3/2007 | Wallace et al. |
| 2008/0221577 A1 * | 9/2008 | Elghazaly .................. 606/64 |
| 2008/0249580 A1 * | 10/2008 | Evans et al. ............... 606/86 R |

FOREIGN PATENT DOCUMENTS

| | | |
|---|---|---|
| JP | 2005/278819 | 10/2005 |
| JP | 2005/279140 | 10/2005 |
| WO | 03/032852 | 4/2003 |
| WO | 2007/038560 | 4/2007 |
| WO | 2008/064059 | 5/2008 |

* cited by examiner

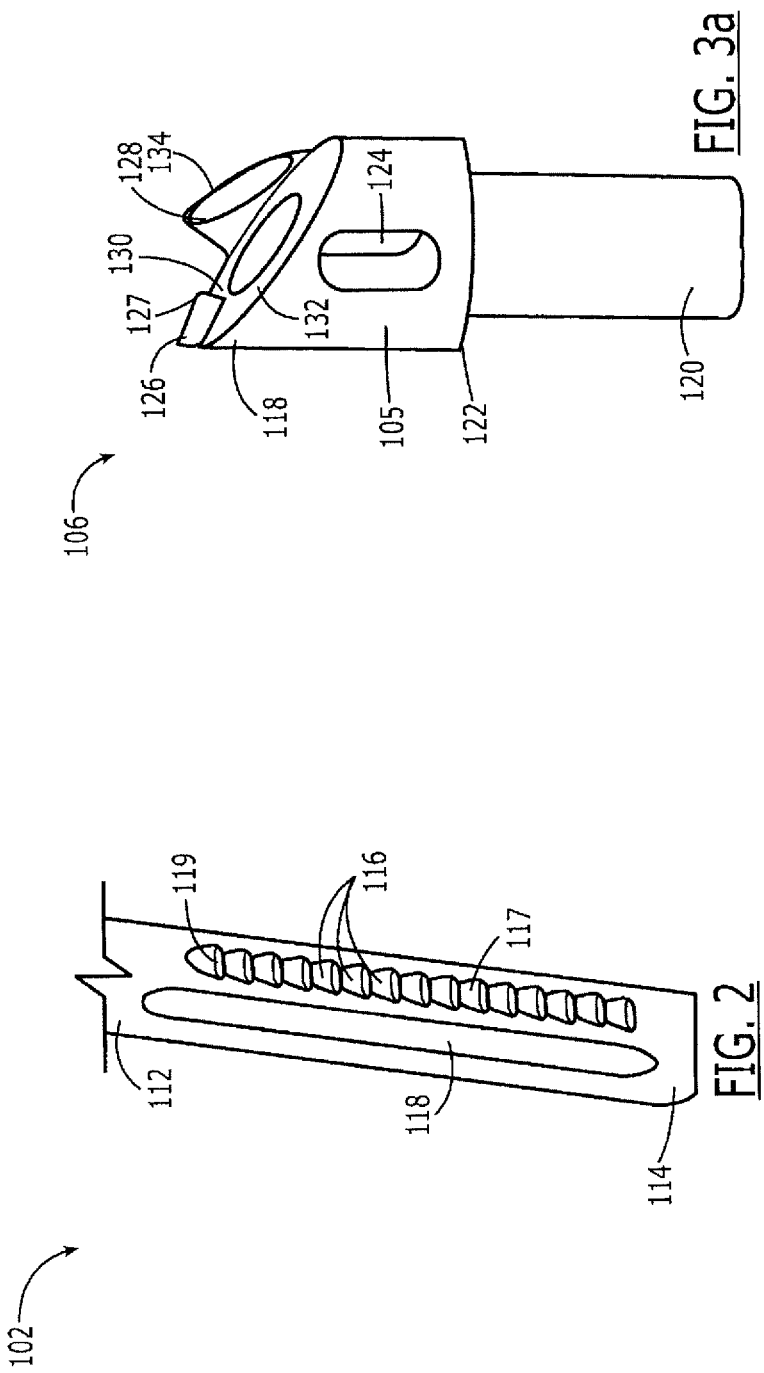

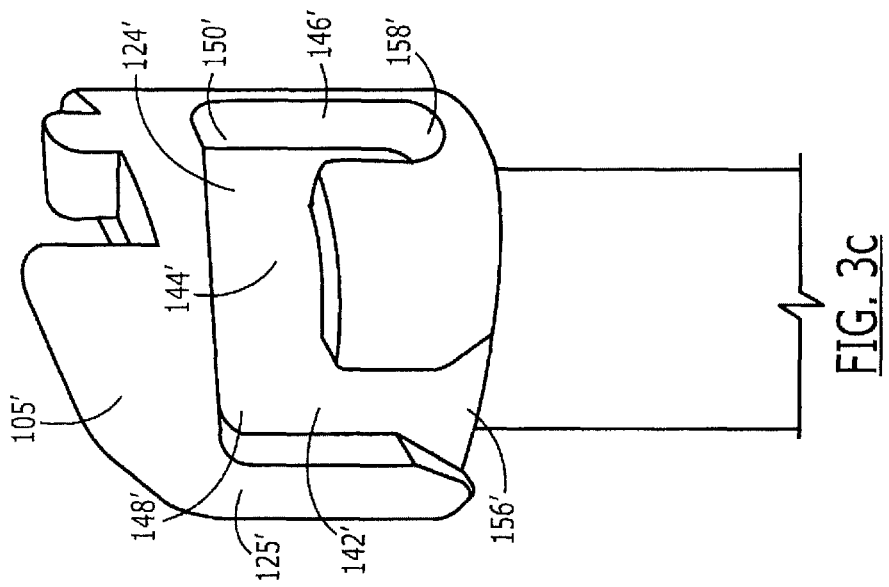
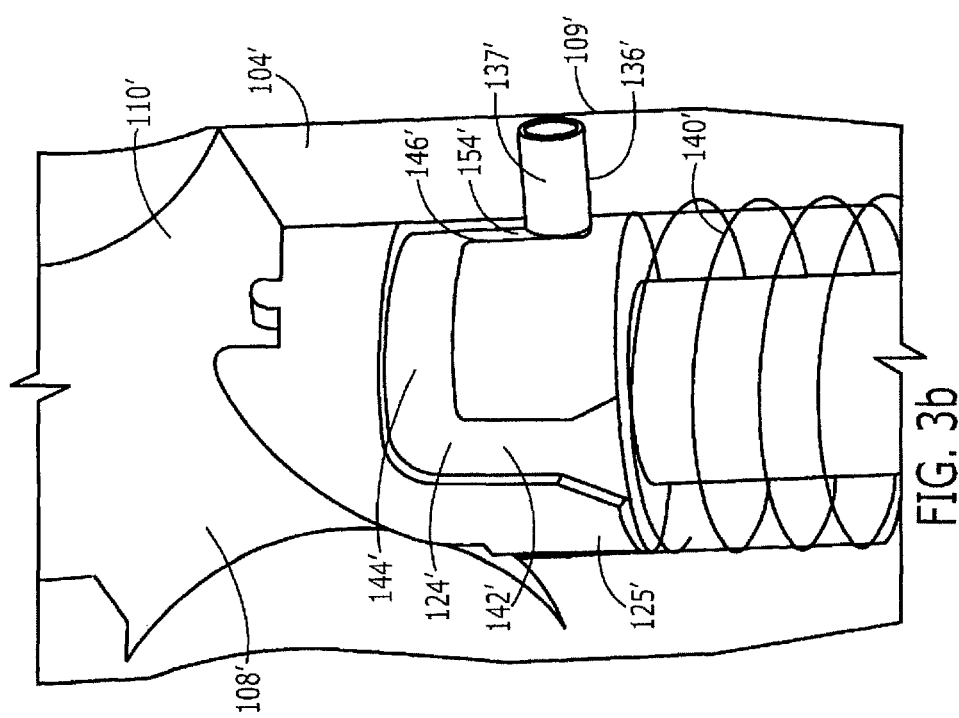

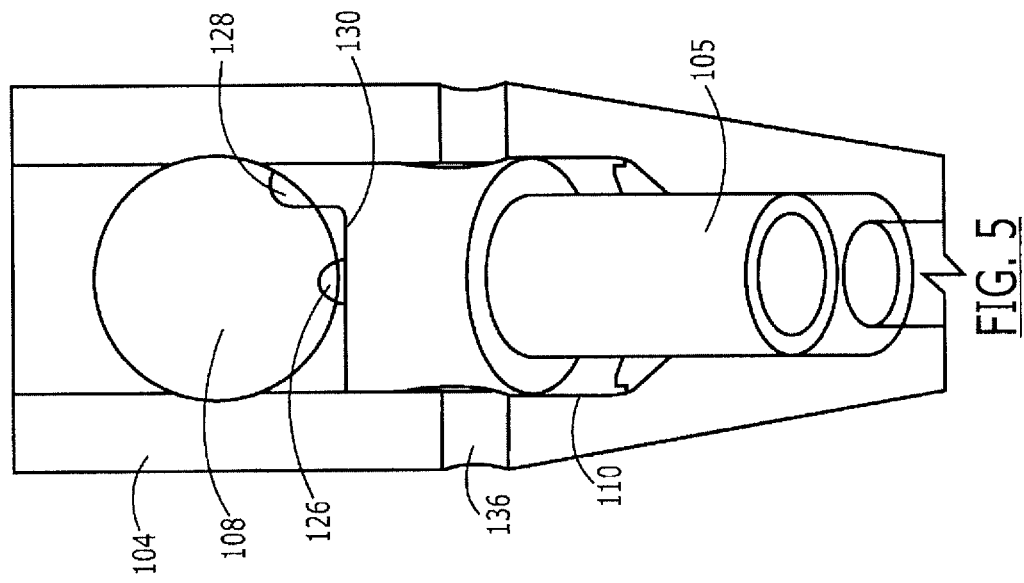
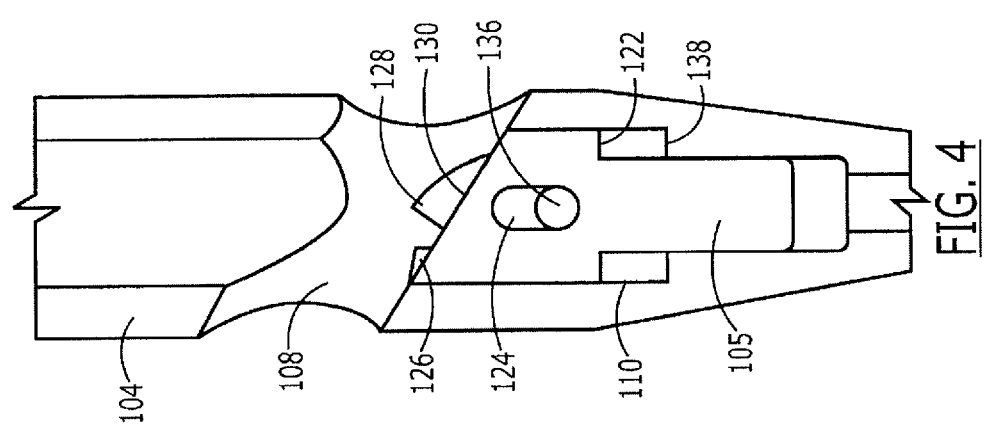

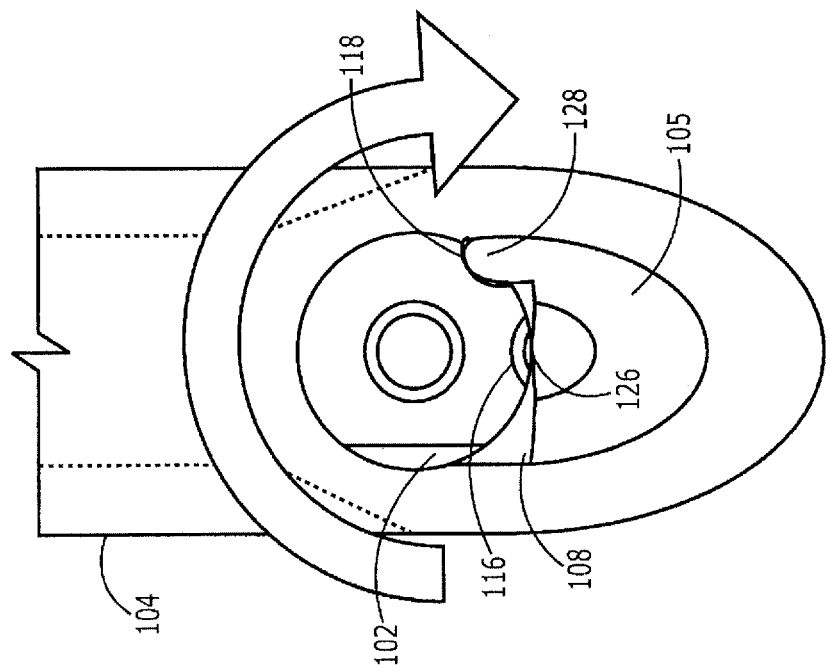
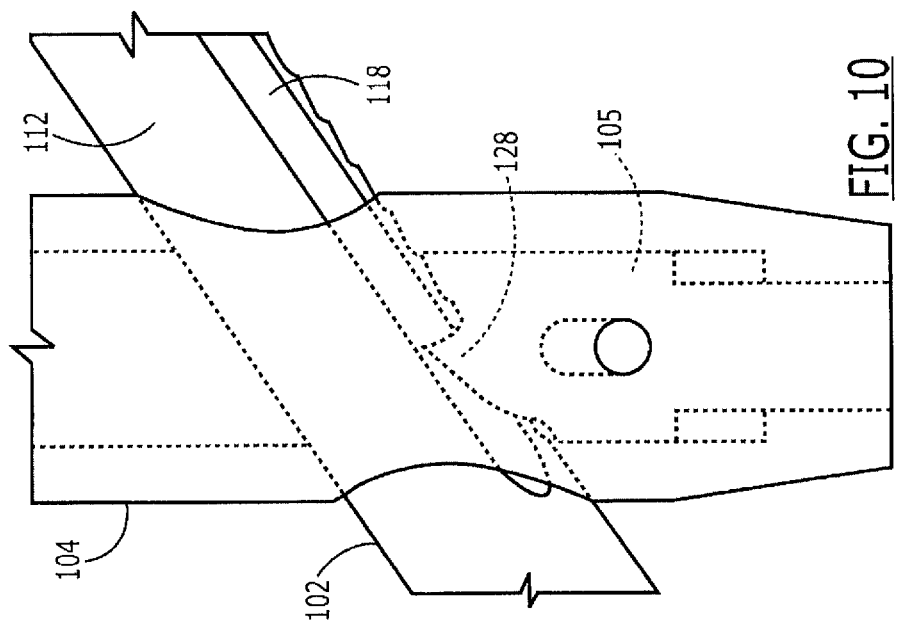

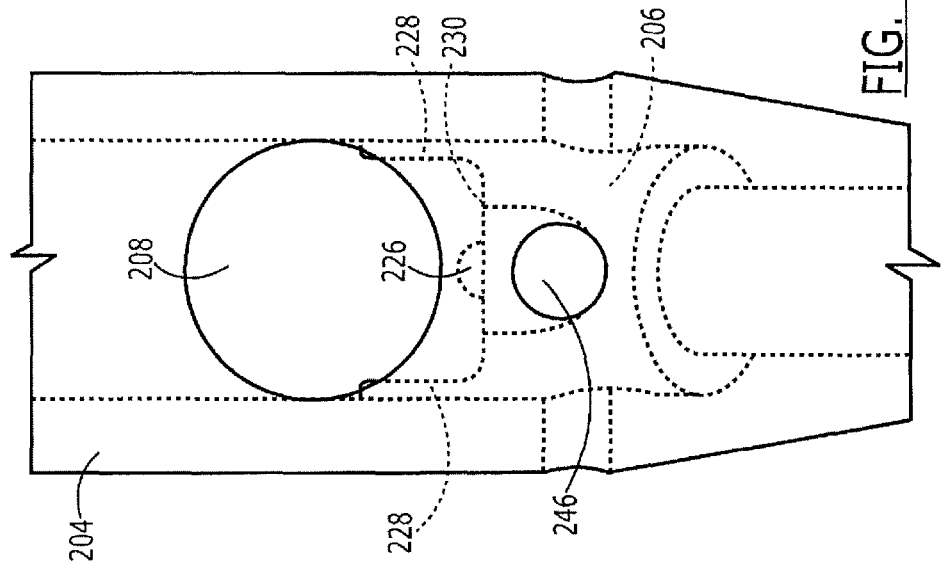
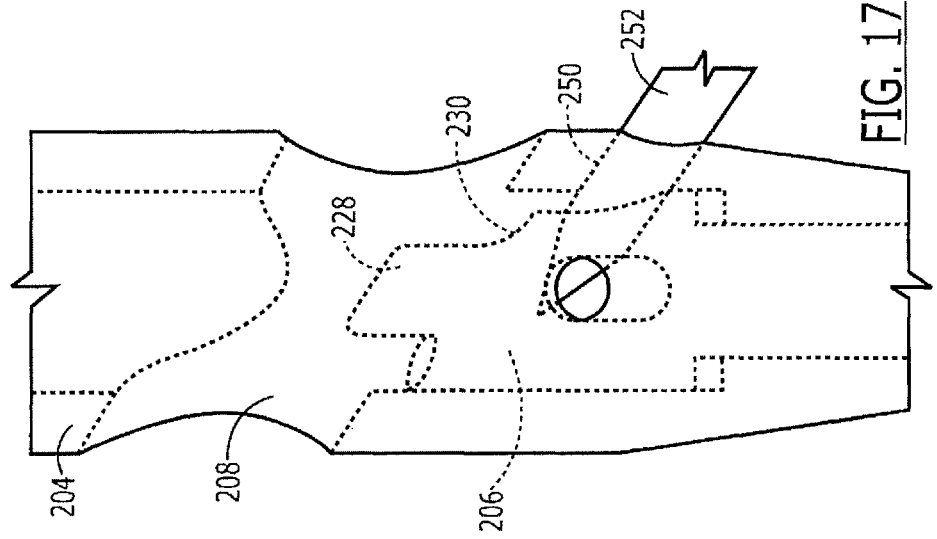

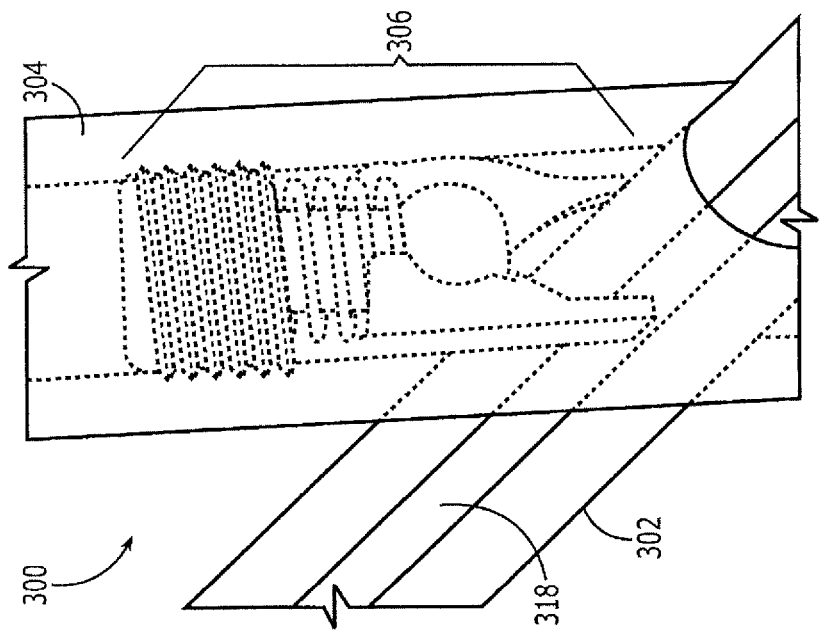
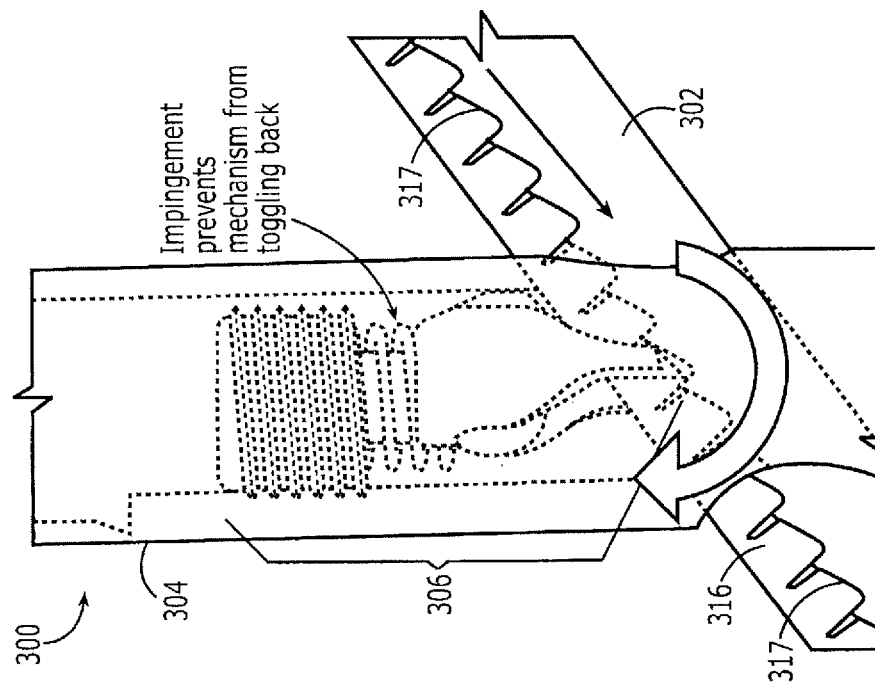

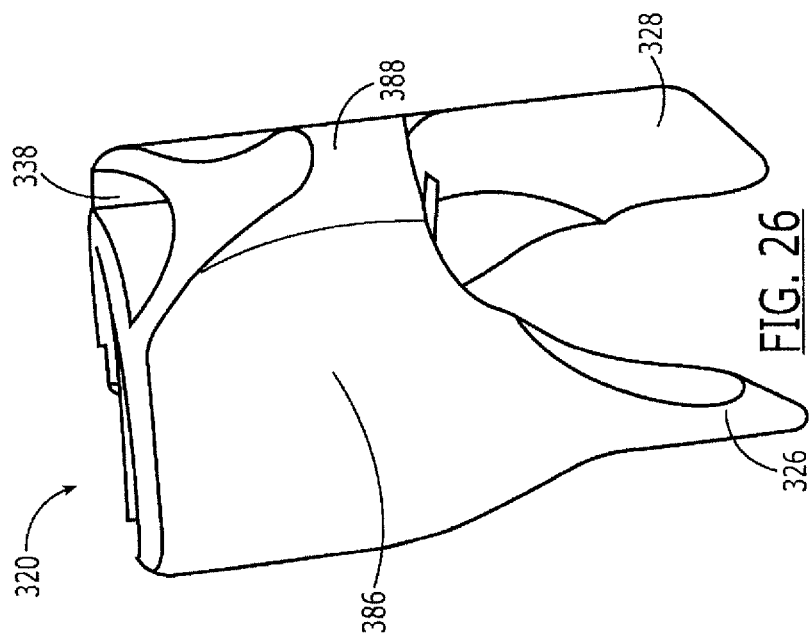
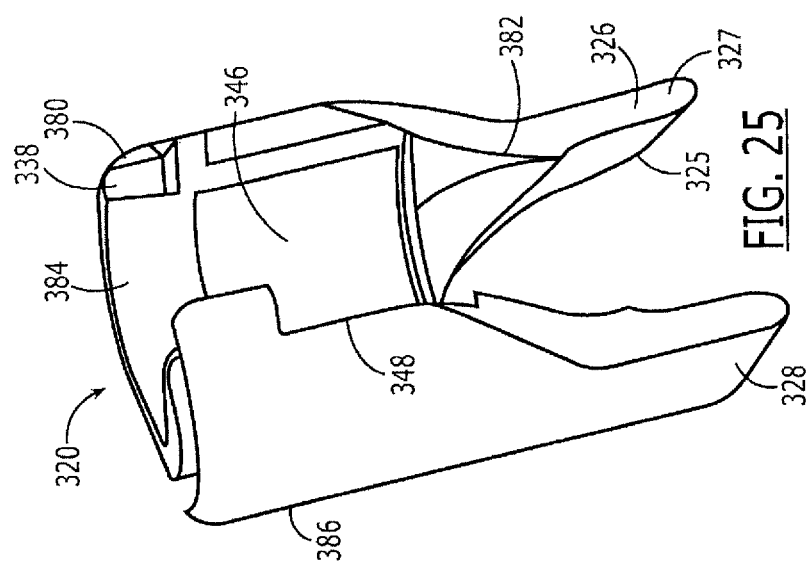

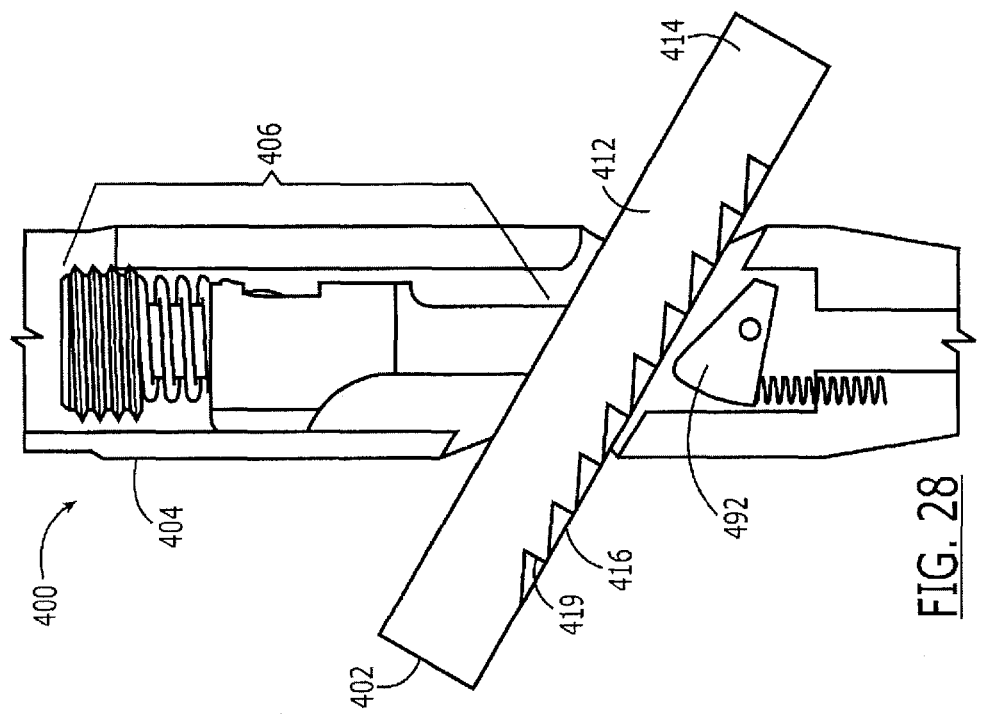
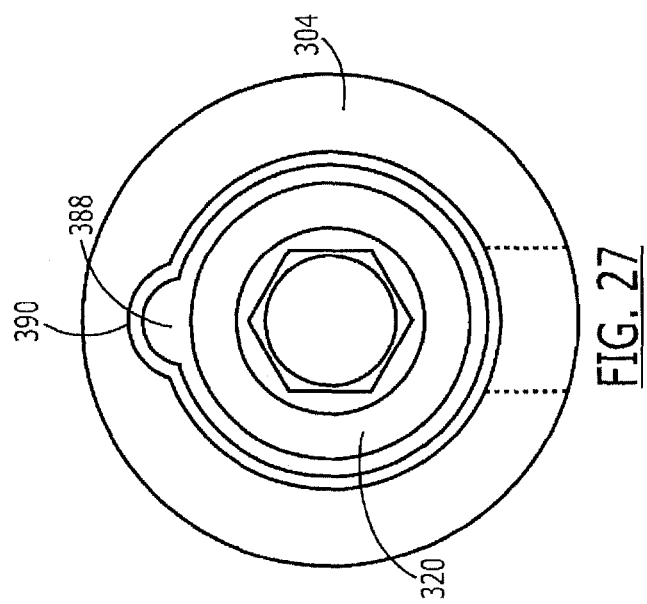

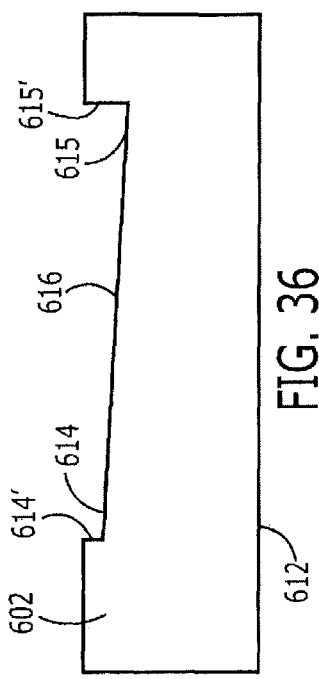
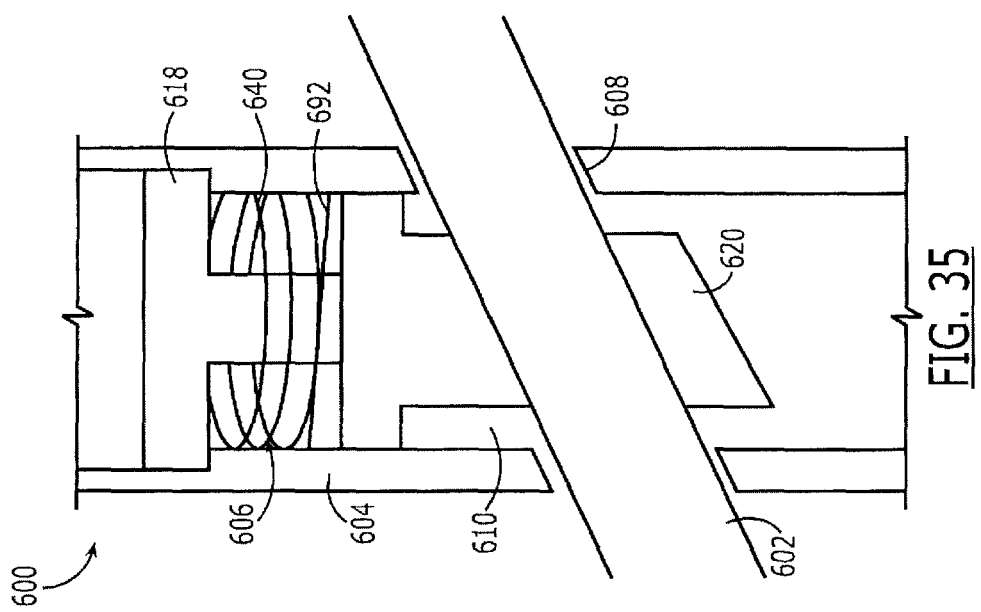

ONE WAY SLIDING DEVICE FOR INTRAMEDULLARY INTERTROCHANTERIC FIXATION IMPLANTS

PRIORITY CLAIM

The present application claims priority to U.S. Provisional Application Ser. No. 61/111,825 filed on Nov. 6, 2008 and entitled "One Way Sliding Device for Intramedullary Intertrochanteric Fixation Implants," the entire disclosure of which is incorporated herein by reference.

FIELD OF THE INVENTION

The present invention relates to devices for treating fractures of long bones and, in particular, to internal fixation devices.

BACKGROUND

Fractures commonly occur in the femur, for example in the femoral neck, intertrochanteric and peritrochanteric regions. Such fractures may be fixed with an intramedullary device and an implant. As is understood by those skilled in the art, the intramedullary device (e.g., an intramedullary nail) is positioned in the medullary canal of a long bone such as the femur. An implant, which may be formed as a helical blade or a lag screw, may then be inserted laterally through bone to pass through an opening of the intramedullary device until a free end of the implant enters the head of the bone. For example, where the bone is a femur, the implant passes through the shaft of the femur, through the intramedullary device and into the femoral head via the neck of the femur to secure the femoral head to a remaining portion of the femur. After implantation, such an implant may move laterally relative to the intramedullary nail along the path over which it was inserted. Some lateral movement of the implant is expected. However, in some cases, the implant may migrate medially through the intramedullary device, resulting in a protrusion through the femoral head and into the acetebulum causing complications.

SUMMARY OF THE INVENTION

The present invention is directed to a device for treating fractures, comprising an intramedullary member sized and shaped for insertion along a longitudinal axis of a bone within a medullary canal thereof, the intramedullary member including an opening extending obliquely therethrough, the opening, when the intramedullary member is in a desired position within a bone, aligning with a desired axis along which an implant is to be inserted into the bone, the intramedullary member including a channel formed therewithin and opening to the opening and a locking mechanism mounted in the channel, the locking mechanism including a locking abutting structure extending into the opening in combination with an implant sized to be slidably received through the opening and inserted along the desired axis, the implant including a plurality of implant abutting structures aligned to engage the locking abutting structure preventing medial movement of the implant relative to the intramedullary member.

The present invention is further directed to a method comprising inserting an intramedullary member into a medullary canal of a bone and inserting an implant into a bone via an opening in the intramedullary member, a shaft of the implant including a plurality of abutting structures distributed along a portion of a length of the shaft, each of the abutting structures including an angled lateral surface and a medially-facing abutting surface in combination with moving a locking mechanism to a locked configuration in which a pawl of the locking mechanism extends into the opening to engage the abutting surface of one of the abutting structures corresponding to a desired medial-most position of the implant, the angled lateral surfaces of the abutting structures permitting lateral movement of the implant relative to the pawl.

BRIEF DESCRIPTION OF THE DRAWINGS

FIG. 2 shows a side view of a distal facing surface of an implant of the device of FIG. 1;

FIG. 3a shows a perspective view of a locking mechanism of the device of FIG. 1;

FIG. 3b shows a perspective view of a locking mechanism and an intramedullary device according to an alternate embodiment of the present invention;

FIG. 3c shows a perspective view of the locking mechanism of FIG. 3b;

FIG. 4 shows a side view of an intramedullary nail and the locking mechanism the device of FIG. 1, in a first configuration;

FIG. 5 shows a perspective view of the intramedullary nail and the locking mechanism of FIG. 4;

FIG. 10 shows an opposite side view of FIG. 9;

FIG. 11 shows a lateral cross-section of the device of FIG. 1;

FIG. 17 shows a side view of the intramedullary nail and the locking mechanism of the device of FIG. 12, in a second configuration;

FIG. 18 shows a perspective view of the intramedullary nail and the locking mechanism of FIG. 17;

FIG. 19 shows a perspective view of a device according to a third exemplary embodiment of the present invention;

FIG. 20 shows another perspective view of the device of FIG. 19;

FIG. 25 shows a perspective view of a second element of the locking mechanism of FIG. 21;

FIG. 26 shows another perspective view of the second element of FIG. 25;

FIG. 27 shows a lateral cross-section of an intramedullary nail and locking mechanism of the device of FIG. 19;

FIG. 28 shows a side view of a device according to a fourth exemplary embodiment of the present invention;

FIG. 35 shows a side view of a device according to a fifth exemplary embodiment of the present invention;

FIG. 36 shows a side view of an implant of the device of FIG. 35;

DETAILED DESCRIPTION

Figure 1:
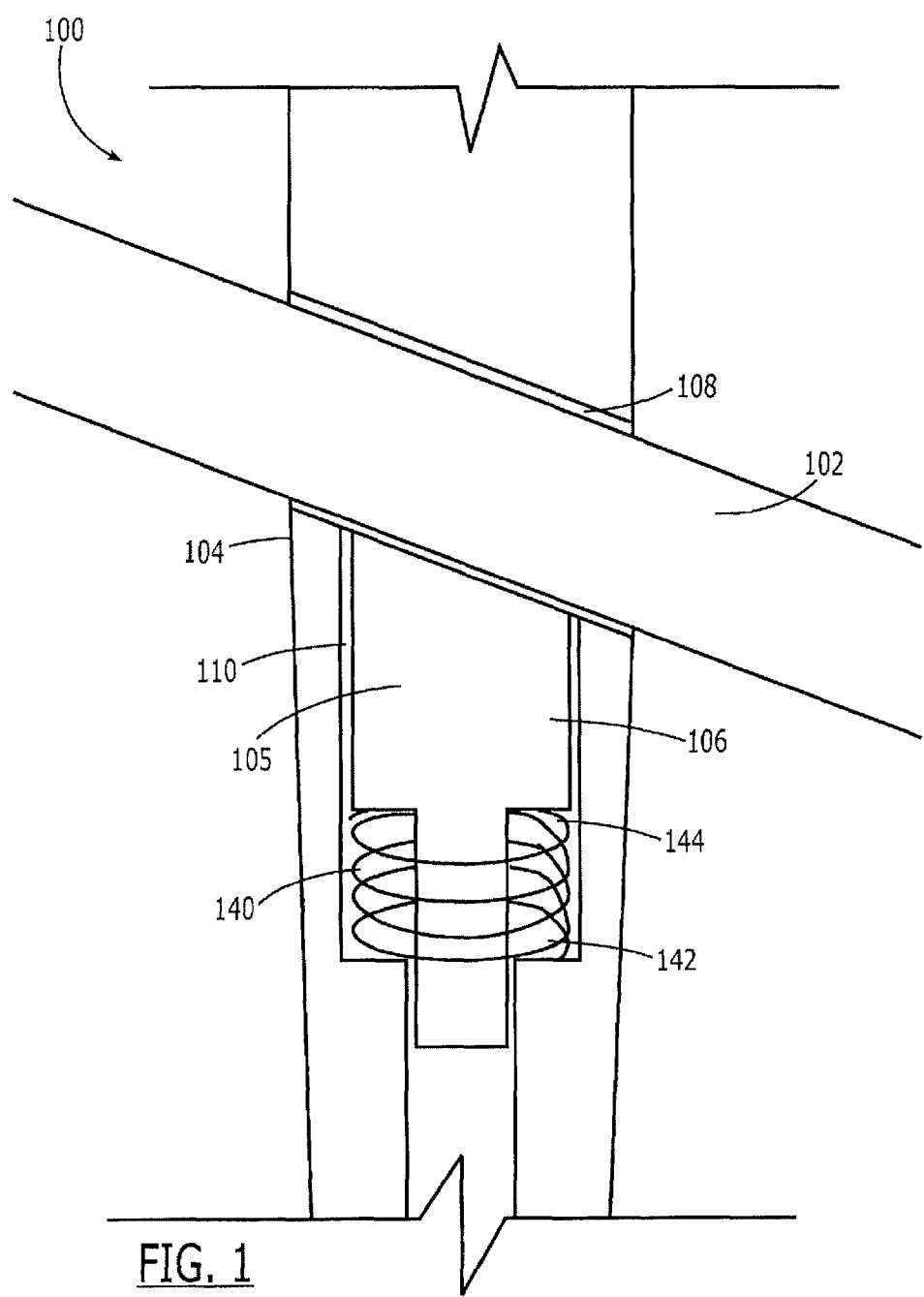
FIG. 1 shows a side view of a device according to a first exemplary embodiment of the invention.
Figure 7:
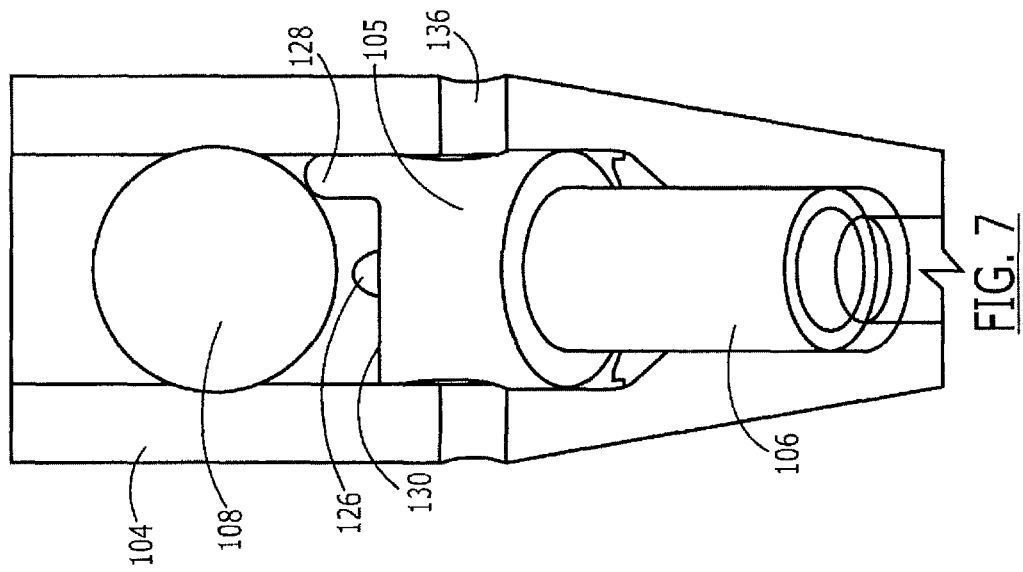
FIG. 7 shows a perspective view of the intramedullary nail and the locking mechanism of FIG. 6.
Figure 6:
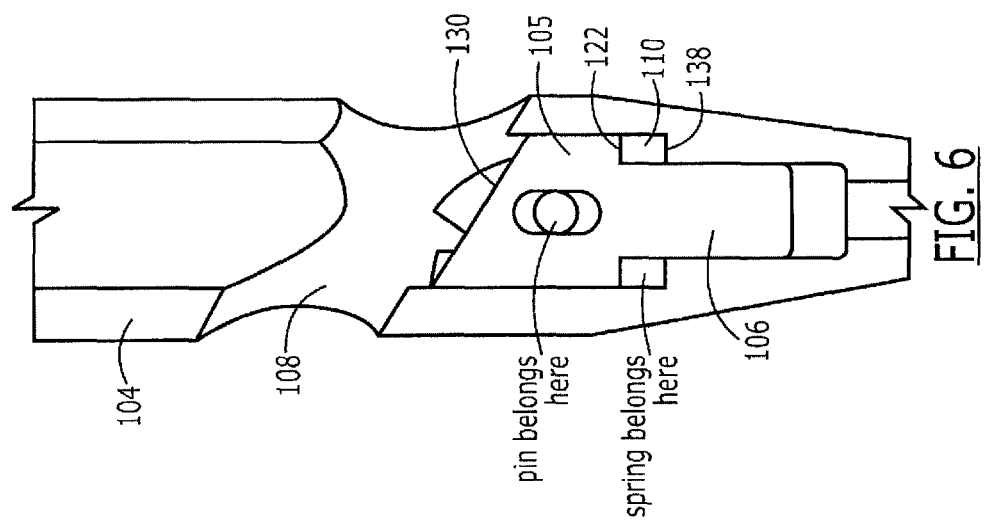
FIG. 6 shows a side view of the intramedullary nail and the locking mechanism of the device of FIG. 1, in a second configuration.
Figure 9:
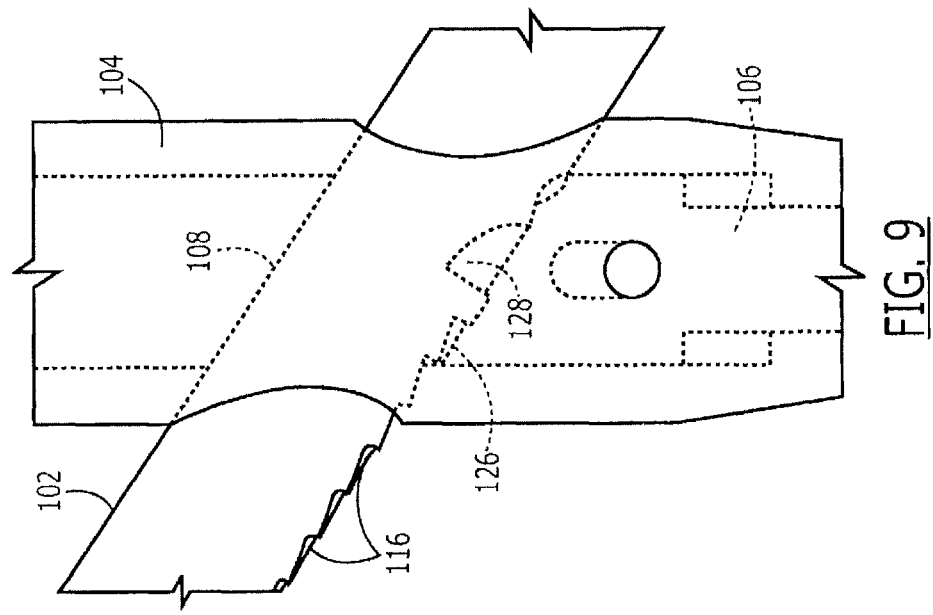
FIG. 9 shows a side view of the device of FIG. 1.
Figure 8:
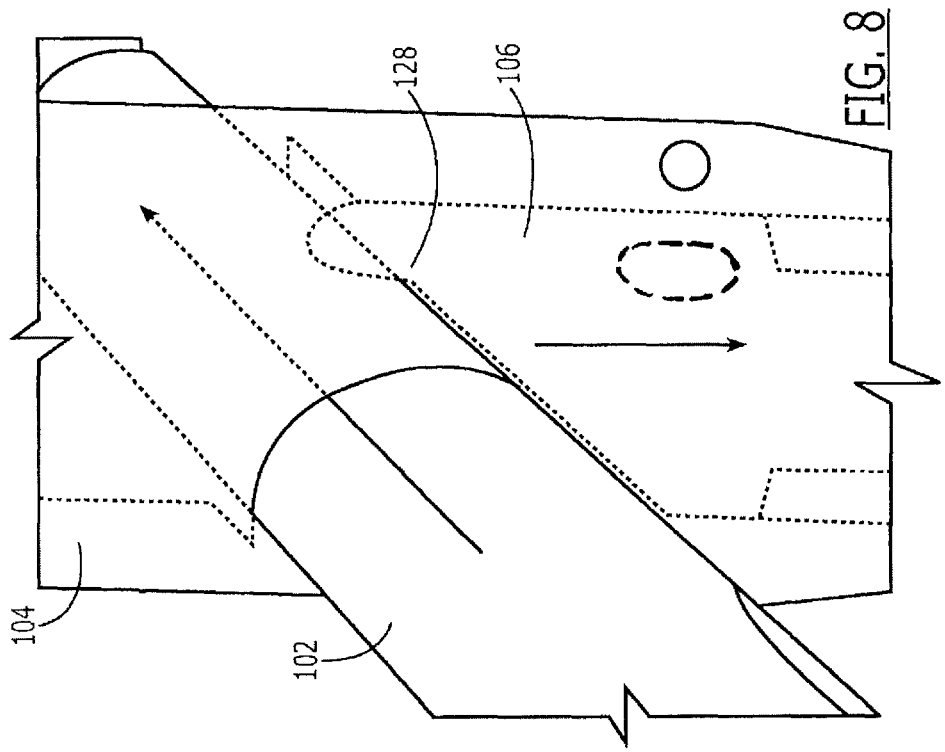
FIG. 8 shows a perspective view of the device of FIG. 1.

The present invention may be further understood with reference to the following description and the appended drawings, wherein like elements are referred to with the same reference numerals. The present invention relates to devices for treating fractures of long bones and, in particular, to internal fixation devices. It is noted that although exemplary embodiments of the present invention are described below with respect to the treatment of fractures of the femur, the invention is not intended to limit the application of the invention to such fractures, as the invention may also be employed in the treatment of other fractures such as, for example, the humerus, tibia, etc. It should also be noted that the terms distal and proximal, used herein, refer to a direction toward (proximal) and away from (distal) a user of the device. As indicated above, fractures of long bones, particularly fractures in which a break is formed between a trochanteric head and a shaft of the bone, may be treated by implanting an intramedullary device along an axis of the shaft of the bone (i.e., in the medullary canal). An implant may then be inserted laterally through the bone to pass through the intramedullary device into the trochanteric head. Devices according to the present invention are designed to permit a desired degree of migration of the implant back toward the point through which it was inserted into the bone (i.e., lateral migration) while minimizing migration of the implant further into the trochanteric head toward the acetebulum (i.e., medial migration).

As shown in FIGS. 1-11, a device 100 according to an exemplary embodiment of the present invention comprises an implant 102 and an intramedullary nail 104 including a locking mechanism 106 (e.g., a ratchet mechanism) permitting limited migration of the implant 102 through the nail 104 laterally while preventing medial migration. As shown in FIG. 1, an oblique opening 108 extending through the nail 104 in a plane substantially perpendicular to a longitudinal axis of the nail 104. The opening 108 is sized to receive the implant 102 therethrough. A channel 110 extending through a portion of the nail 104 along the longitudinal axis opens to the opening 108 houses the locking mechanism 106. In the embodiment shown, the channel 110 and the locking mechanism 106 extend distally of the opening 108 so that the locking mechanism 106 engages a distal side of the implant 102 when the implant 102 is inserted through the oblique opening 108. Those skilled in the art will understand that the channel 110 and the locking mechanism 106 may alternatively be located on the proximal side of the implant 102. The locking mechanism 106 includes a biasing member 140 (e.g., a spring) engaging a pawl member 105 to urge the pawl member 105 into contact with the implant 102.

As shown in FIG. 2, a distal facing surface of a locking engaging portion of the implant 102 which, when assembled in a desired configuration, overlaps with the channel 110 includes features for engaging corresponding structures of the pawl member 105. Specifically, the implant 102 comprises a shaft 112 extending from a proximal end 114 to a distal end (not shown) coupled to the proximal end of a blade or other bone engaging structure (not shown). As would be understood by those skilled in the art, the bone engaging structure may be formed as a helical blade extending distally from the distal end of the shaft 112. It will be understood by those of skill in the art however, that the bone engaging structure may be any other fixation means such as, for example, a lag screw.

The locking engaging portion of the shaft 112 includes a plurality of abutting structures 116 spaced from one another along a portion of a length of the shaft 112. Each of the abutting structures 116 includes a ramped surface 117 extending from a position adjacent to a radially inner end of the abutting structure 116 immediately distal thereto and angling gradually outward to an abutting surface 119. As would be understood by those of skill in the art, the abutting surfaces 119 of the abutting structures 116 may extend substantially perpendicular to a longitudinal axis of the implant 102.

As shown in FIG. 3a, the pawl member 105 includes an implant engaging surface 130 angled to substantially align with an angle of the opening 108. A pawl 126 including a proximally facing abutting surface 127 extends out from the surface 130 so that, when in an operational position, the abutting surface 127 of the pawl 126 engages an abutting surface 119 of one of the abutting structures 116 of the implant 102. Thus, engagement between the pawl 126 and the abutting structure 116 of the shaft 112 prevents movement of the implant 102 medially relative to the nail 104. However, the implant 102 may slide laterally as the angled distal surface of the pawl 126 and the angled surfaces 117 of the abutting structures 116 allow the shaft 112 to slide laterally over the pawl member 105. A protrusion 128 including a ramped surface 134 extends outward from the implant engaging surface 130 by a distance greater than the pawl 126 so that, during insertion of the implant 102 through the opening 108, contact between the shaft 112 and the protrusion 128 moves the locking engaging portion of the shaft 112 out of contact with the pawl 126 until the implant 102 has been advanced to a desired position in the bone. When in the desired position, the implant 102 is rotated about its longitudinal axis to a locking orientation in which the protrusion 128 aligns with and enters a groove 118 formed in the shaft 112. At this point, the abutting structures 116 of the shaft 112 and the pawl 126 are aligned with one another so that, as the implant 102 moves toward the pawl member 105 due to the insertion of the protrusion 128 into the groove 118, the pawl 126 engages one of the abutting structures 116 corresponding to the desired medial-most position of the implant 102. As described above, engagement between the abutting surface 127 of the pawl 126 and the abutting surface 119 of the abutting structure 116 prevents further medial migration of the implant 102. This contact between the pawl member 126 and the corresponding abutting structure 116 is maintained by the biasing member 140 which urges the pawl member 105 toward the shaft 112 at all times.

To ensure that the locking mechanism 106 does not move beyond the first and the second configuration, the locking mechanism 106 may also include an elongated hole 124 extending laterally through the locking mechanism 106, distally of the shoulder 122, for receiving a pin (not shown) which fixes the locking mechanism 106 to the intramedullary nail 104. Thus, the intramedullary nail 104 also includes a hole 136 extending laterally therethrough, distally of the oblique opening 108 such that the position of the hole 136 corresponds to a position of the elongated hole 124. The hole 136 may be substantially circular such that the intramedullary nail 104 remains stationary while the locking mechanism 106 moves relative to the intramedullary nail 104 along the longitudinal axis. It will be understood by those of skill in the art that the pin inserted through the holes 124, 136 fixes the locking mechanism 106 to the intramedullary nail 104 such that the locking mechanism 106 and the intramedullary nail 104 may not rotate relative to one another, but may move between the first configuration and the second configuration along the longitudinal axis of the intramedullary nail 104.

In an alternative embodiment, as shown in FIGS. 3b-3c, a locking mechanism 106' may include a pawl member 105' formed with a recess 124' rather than an elongate hole for fixing the locking mechanism 106' within an intramedullary nail 104'. The recess 124' may be fixed within the intramedullary nail 104' via a pin 137' that is inserted into the intramedullary nail 104' and the recess 124'. The locking mechanism 106' is substantially similar to the locking mechanism 106 and may be used in the device 100 in substantially the same manner. The recess 124' may be formed on an outer surface 125' of the pawl member 105' and may include a first portion 142', a second portion 144' and a third portion 146'. The first portion 142' extends longitudinally along a portion of the outer surface 125' from an edge 156' of the pawl member 105' to a proximal end 148' of the first portion 142'. The second portion 144' extends substantially horizontally along a portion of the outer surface 125' from the proximal end 148' of the first portion 142' to an opposite end 150'. The third portion 146' extends from the end 150' longitudinally along the outer surface 140' in a distal direction. The first portion 142', the second portion 144' and the 146' are connected such that they form a single continuous recess 124'.

The intramedullary nail 104' includes a hole 136' extending laterally through one side of the intramedullary nail 104', distally of an oblique opening 108' such that a positioning of the hole 136' corresponds to position of the recess 124'. The hole 136' is adapted and configured to receive the pin 137' therethrough. A length of the pin 137' may be slightly longer than a thickness of the intramedullary nail 104'. The thickness is determined by a distance from an outer surface 109' of the intramedullary nail 104' to a channel 110' of the intramedullary nail 104', which extends longitudinally therethrough. Thus, when the pin 137' is inserted through the hole 136' such that a proximal end 152' of the pin 137' is flush with the outer surface 109', a distal end 154' of the pin 137' extends into the channel 110' for engaging the recess 124'. The hole 136' may be substantially circular such that the intramedullary nail 104 remains substantially stationary while the locking mechanism 106' moves relative to the intramedullary mail 104' along the longitudinal axis.

To fix the locking mechanism 106' within the intramedullary nail 104', a biasing member 140' of the locking mechanism 106' may be inserted into the channel 110' along with the pawl member 105' such that the biasing member 140' urges the pawl member 105' into a position of contact with an implant (not shown) that is inserted into the opening 108'. The pawl member 105' is inserted distally into the channel 110' until the distal end 154' of the pin 137' that is inserted into the hole 136' engages the first portion 142' of the recess 124' via the edge 156' of the first portion 142'. The pawl member 105' is pressed further distally against the urging of the biasing member 140' such that the first portion 142' slides along the pin 137' until the proximal end 148' of the first portion 142' is in contact with the pin 137. The pawl member 105' may then be rotated about a longitudinal axis thereof such that the second portion 144' slides along the pin 137' until the pin 137' is contacting the opposite end 150' of the second portion 144'. Upon reaching the opposite end 150', the pawl member 105' may be released, the biasing member 140' urging the pawl member 105' in a proximal direction such that the third portion 146' slides along the pin 137' until the pin 137' engages a distal end 158' of the third portion 146'. Thus, it will be understood by those of skill in the art that once the locking mechanism 106' is fixed within the intramedullary nail 104', the locking mechanism 106' is movable along the longitudinal axis to engage the implant, as described in regard to the device 100. Longitudinal movement of the locking mechanism 106' results in sliding of the third portion 146' longitudinally along the distal end 154' of the pin 137'.

In a first configuration, shown in FIGS. 4-5, when no implant 102 is present in the opening 108, the implant engaging surface 130 substantially aligns with a wall of the oblique opening 108 while the pawl 126 and the protrusion 128 extend into the oblique opening 108. Then, as an implant 102 is inserted into the opening 108, contact between the implant 102 and the ramped surface 134 forces the pawl member 105 into the channel 110 to a second configuration in which the protrusion 128 is moved into the channel 110 to a second configuration shown in FIGS. 6 and 7 to allow the implant 102 to be advanced medially through the opening 108. The pawl member 105 is constrained so that it does not move further into the opening 108 than desired (i.e., beyond a desired first configuration), by a pin 135 passing through an opening 136 in the intramedullary nail 104, and through an elongated opening 124 in the pawl member 105. As described above, when the implant 102 has been inserted to a desired position in the bone, the implant 102 is rotated about its axis until the groove 118 aligns with the protrusion 128. At this point the biasing member 140 moves the pawl member 105 back to the first configuration with the protrusion 128 received within the slot 118 and the pawl 126 engaging one of the abutting structures 116 of the implant 102 corresponding to the desired maximum insertion of the implant 102 into the bone. Thereafter, as forces are applied to the implant 102 (e.g., as weight is placed on the bone), the implant 102 may move laterally as ramped surfaces 117 slide over the pawl 126. The abutting surface 119 engages the pawl 126 preventing any further movement medially. In addition, as each abutting surface 119 moves laterally past the pawl 126, a new medial-most position of the implant 102 is defined.

The intramedullary nail 104 may further include a shoulder 138 within the channel 110 positioned below the oblique opening 108. A reduced diameter shaft 120 extends from an end of the pawl member 105 to a shoulder 122 at an end of an upper portion of the pawl member 105. The biasing member 140 is received between the shoulder 122 and the shoulder 138 of the channel 110 to urge the pawl member 105 toward the opening 108. A diameter of a portion of the channel 110 closer to the opening 108 than the shoulder 138 is larger than a diameter of the portion of the channel 110 extending past the shoulder 138 away from the opening 108. It will be understood by those of skill in the art that the diameters of these portions the channel 110 correspond to the diameters of the proximal end 118 of the pawl member 105 and the shaft 120, respectively.

In use, the intramedullary nail 104 is inserted into an intramedullary canal (e.g., of a femur) with a central axis of the oblique opening 108 substantially aligned with a central axis of the femoral neck. It will be understood by those of skill in the art that the intramedullary nail 104 may be inserted into the bone using any accepted insertion method. For example, a guidewire may be inserted into the medullary canal of the longitudinal shaft and the intramedullary nail 104 slid therealong. Thus, it will also be understood by those of skill in the art that the intramedullary nail 104 and the locking mechanism 106 housed therewithin may also include a guide wire lumen along the longitudinal axis thereof. Once the intramedullary nail 104 has been appropriately positioned, the implant 102 is inserted through the bone into the oblique opening 108 to a desired position and the implant 102 is rotated to return the locking mechanism 106 to the first configuration preventing further medial movement as described above.

If it becomes necessary to remove the implant 102 for any reason, however, the implant 102 may be rotated about the central axis of the oblique opening 108, as shown in FIG. 11 to move the protrusion 128 out of the groove 118 and force the pawl member 105 back to the first configuration. At this point the locking mechanism 106 is disengaged from the abutting structures 116 of the implant 102 and the implant 102 may be slid entirely out of the opening 108 even after the protrusion 128 is located distally beyond the distal end of the groove 118. If the bone engaging structure of the implant 102 is formed as a helical blade, those skilled in the art will understand that this structure may be rotatably coupled to the shaft 112 of the implant 102 so that the engagement between the locking mechanism 106 and the abutting structures 116 of the implant 102 is maintained. Thus, any rotation of the helical blade during insertion would not require a corresponding rotation of the shaft 112. However, it will be understood by those of skill in the art that the bone engaging structure of the implant 102 may be any known capable of securing the femoral head and neck to the shaft through engagement of an intramedullary nail 104.

Figure 12:
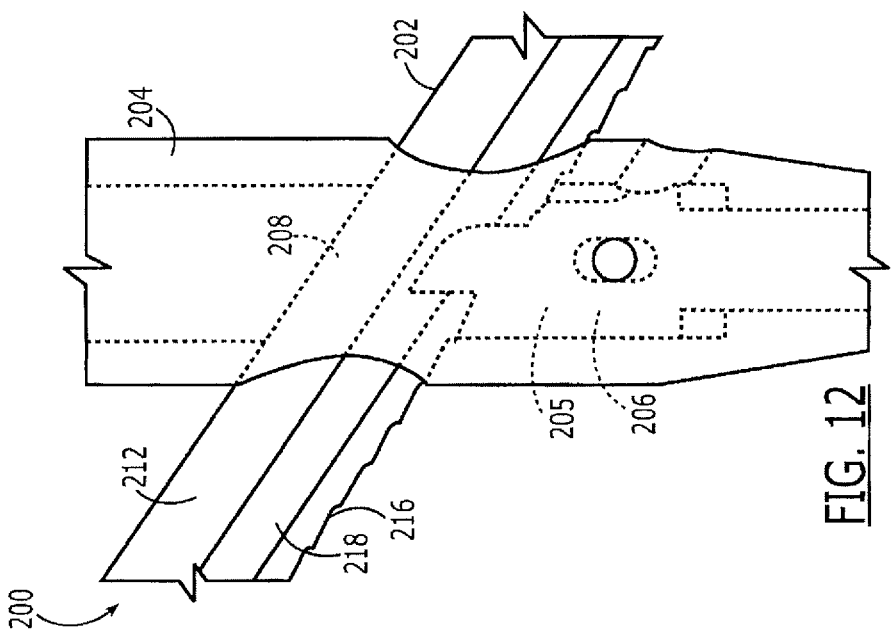
FIG. 12 shows a side view of a device according to a second exemplary embodiment of the present invention.

As shown in FIGS. 12-18, a device 200, according to another embodiment of the present invention comprises an implant 202 and an intramedullary nail 204 with a locking mechanism 206 housed therewithin. The device 200, as shown in FIG. 12, is substantially similar to the device 100 described above including a biasing member 240 (e.g., a spring) moving the locking mechanism 206 within a channel 210 of the nail 204 along a longitudinal axis of the nail 204. The locking mechanism 206 also moves between first and second configurations in which a pawl 226 is brought into and out of the opening 208 to engage and disengage abutting structures 216 of the implant 202.

Figure 14:
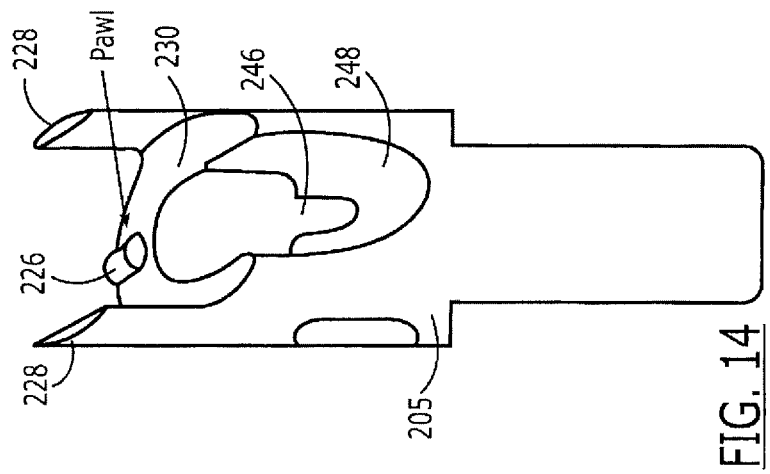
FIG. 14 shows a perspective view of a locking mechanism of the device of FIG. 12.
Figure 13:
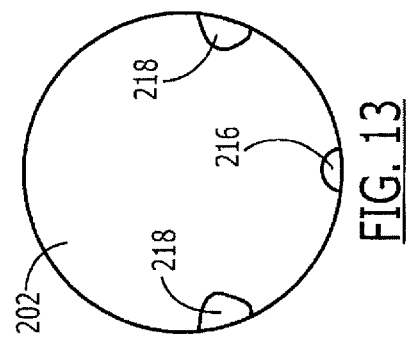
FIG. 13 shows a cross-sectional view of an implant of the device of FIG. 12.

However, the pawl member 205 of the locking mechanism 206 does not include a protrusion similar to the protrusion 128 for engaging the implant 202 and moving the pawl member 205. The implant 202 may be substantially similar to the implant 102 except that no groove similar to the groove 118 is provided. Rather, a shaft 212 of the implant 202 may include a plurality of notches 218 extending longitudinally along a portion of a length thereof and separated from one another around the circumference of the shaft 212 by a distance corresponding to a separation of a pair of notch engaging wings 228 extending from an implant engaging surface 230 of the pawl member 205. Thus a first one of the wings 228 is received within a corresponding one of the notches 218. When the wings 228 are received in the notches 218, the abutting structures 216 of the implant 202 are aligned with the pawl 226 of the pawl member 205. Engagement between the wings 228 and the notches 218 prevents the shaft 212 from rotating within the opening 208. As shown in FIG. 14, the locking mechanism 206 may be substantially similar to the locking mechanism 106 with the pawl 226 extending from the implant engaging surface 230 and engaging the abutting structures 216 to prevent medial movement of the implant 202 beyond a defined medial-most position.

Figure 16:
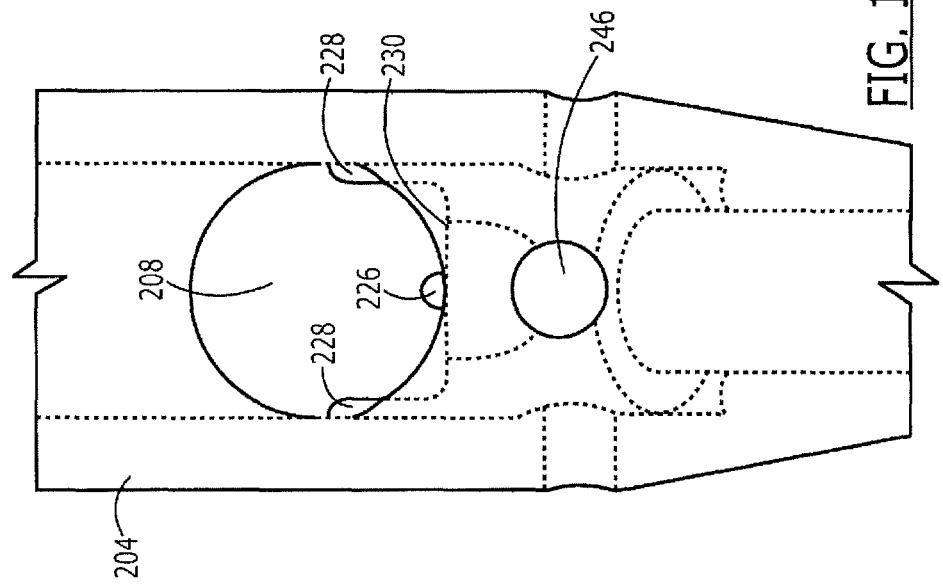
FIG. 16 shows another perspective view of the intramedullary nail and the locking mechanism of FIG. 15.
Figure 15:
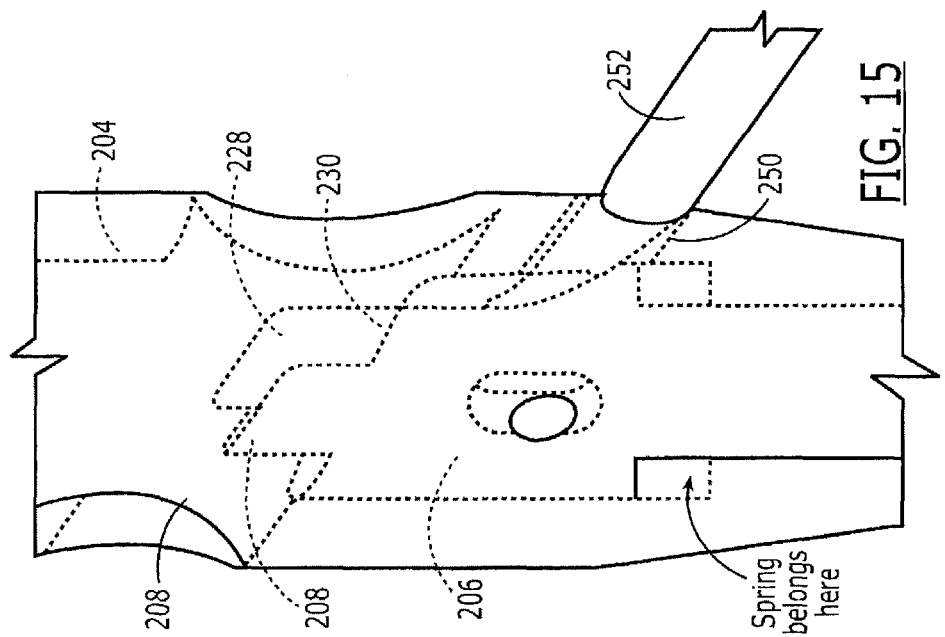
FIG. 15 shows a perspective view an intramedullary nail and the locking mechanism of the device of FIG. 12, in a first configuration.

The locking mechanism 206 includes a laterally facing hole 246 which is aligned with a corresponding opening 250 adjacent to the lateral end of the opening 208 so that a tool may be inserted therethrough to engage the pawl member 205 and move it manually between from the first configuration, shown in FIGS. 15-16, to the second configuration, shown in FIGS. 17-18. The hole 246 may include a ramped surface 248 so that when a pin 252 is inserted into the hole 246 via the hole 250, the pin 252 slidingly engages the ramped surface 248 pushing the pawl member 205 further into the channel 210 disengaging the locking mechanism 206 from the abutting structures 216 to permit insertion and/or withdrawal of the implant 202 from the opening 208 to the second configuration. It will be understood by those of skill in the art that the ramped surface 248 enables the size of the hole 246 to be minimized so that the hole 248 does not need to extend into an elongated hole 224 of the locking mechanism 206 which engages a pin (not shown) in the same manner as the pin 135 of the device 100 to prevent the pawl member 205 from moving into the opening 208 beyond the first configuration.

The device 200 may be employed in substantially the same manner as the device 100 as described above. However, when inserting the implant 202 through the nail 204, the pin 252 is inserted into the hole 246 of the locking mechanism 206 via the hole 250 to move the locking mechanism 206 to the second configuration. The implant 202 is then inserted to the desired position in substantially the same manner described above and the pin 252 is removed to allow the pawl member 205 to return to the first configuration through the bias of the biasing member 240 to lock the locking mechanism 206 to the abutting structures 216 and prevent further medial movement of the implant 202. As with the device 100, the shape of the abutting structures 216 allows the implant 202 to move laterally over the pawl 226.

As shown in FIGS. 19-27, a device 300 according to another embodiment of the invention comprises an implant 302 and an intramedullary nail 304 with a locking mechanism 306 housed therewithin. The device 300, as shown in FIGS. 19-20 is substantially similar to the devices 100, 200 described above except as specifically indicated below. The implant 302 is also substantially similar to the implant 102, including a shaft 312 with a plurality of abutting structures 316 and a longitudinal groove 318. Similarly to the intramedullary nail 104, the intramedullary nail 304 includes an oblique opening 308 for receiving the implant 302. However, a channel 310 of the intramedullary nail 304 in which the locking mechanism 306 is housed extends proximally from the oblique opening 308 toward a proximal end of the intramedullary nail 304.

Figure 22:
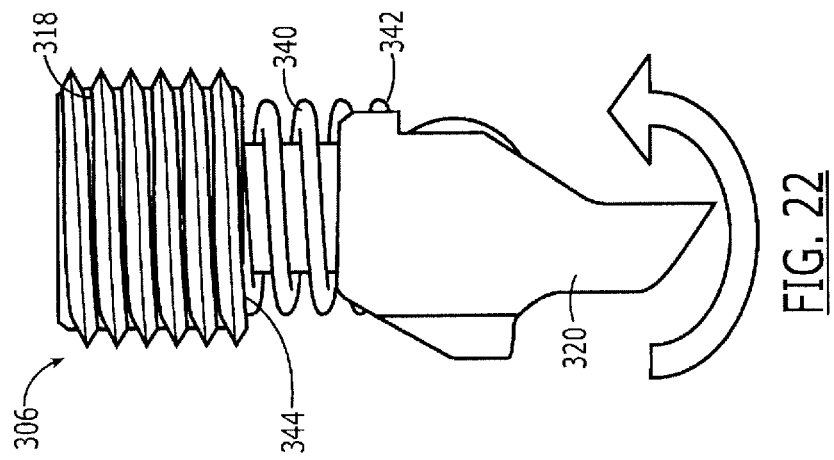
FIG. 22 shows a side of the locking mechanism of FIG. 21.
Figure 21:
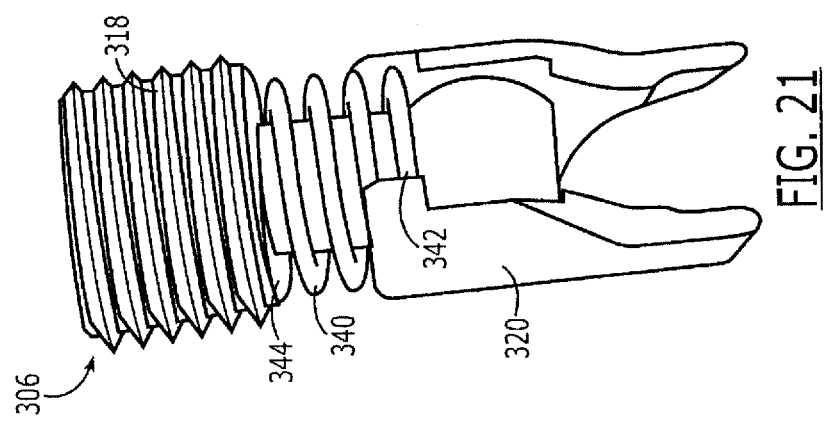
FIG. 21 shows a perspective view of a locking mechanism of the device of FIG. 19.
Figure 23:
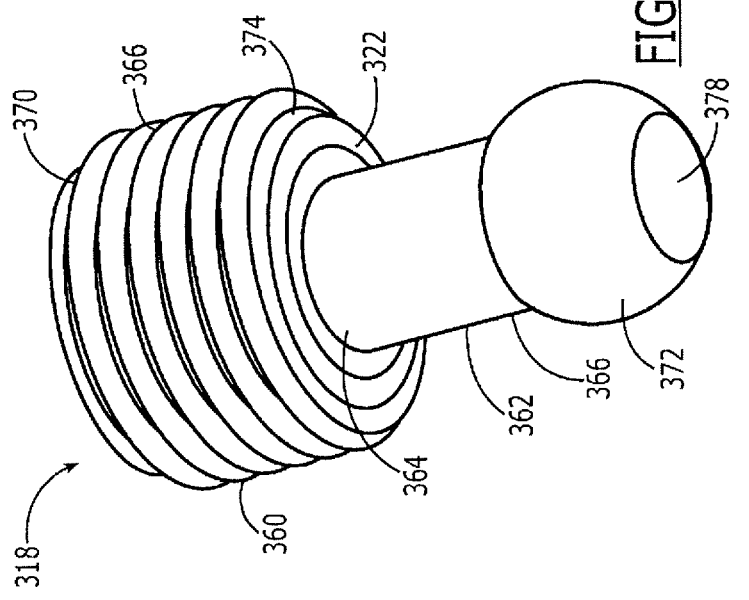
FIG. 23 shows a perspective view of a first element of the locking mechanism of FIG. 21.
Figure 24:
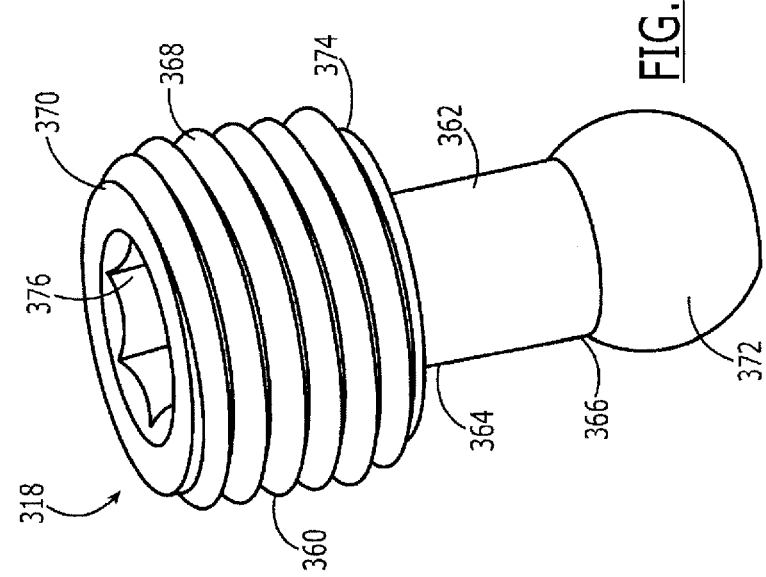
FIG. 24 shows another perspective view of the first element of FIG. 23.

As shown in FIGS. 21-22 a pawl member 305 of the locking mechanism 306 is further comprised of a first element 318 and a second element 320. The first element 318 may be coupled to the second element 320 such that the first element 318 and the second element 320 are movable relative to one another both along and about a longitudinal axis. As shown in FIGS. 23-24, the first element 318 includes a head portion 360, a shaft 362 and a ball 372 at a distal end 366 of the shaft 362 configured to engage a correspondingly shaped recess in the second element 320. A diameter of the ball 372 may be larger than a diameter of the shaft portion 362.

The head portion 360 extends proximally from a proximal end 364 of the shaft 362 and includes threading 368 around an outer surface thereof. The head portion 360 further includes a driving structure 376 at a proximal end 370 thereof configured to receive a driving tool. For example, the driving structure 376 may be a hexagonal recess configured to receive a hexagonally shaped bit of a driving tool. It will be understood by those of skill in the art, however, that the driving structure 376 may take any of a variety of shapes and sizes so long it is configured to receive a tool capable of rotating the first element 318 relative to the second element 320 and the intramedullary nail 304. An annular groove 322 formed in a distally facing surface at a distal end 374 of the head portion 360 receives a proximal end 344 of a biasing member 340 (e.g., a spring). The biasing member 340 may extend around the shaft 362 of the first element 318. The first element 318 may also include a lumen 378 extending longitudinally therethrough, to accommodate instruments such as reaming rods or guidewires, etc.

As shown in FIGS. 25-26, the second element 320 extends from a proximal end 380 to a distal end 382 and includes a space 346 in a central portion thereof sized and shaped to accommodate the ball 372 of the first element 318 to form a ball and socket joint. The proximal end 380 includes a hole 384 that extends into the space 346 to accommodate the shaft portion 362 when the ball 372 is received within the space 346. The second element 320 may further include an opening 348 along a portion of an outer surface 386 of the second element 320 such that the ball 372 may be snapped into the space 346 via the opening 348. The opening 348 should be smaller than a diameter of the ball 372 so that the second element 320 must be slightly deformed to snap the ball 372 thereinto and the ball 372 may not become easily disengaged therefrom.

The distal end 382 includes a first protrusion 326 for engaging the abutting structures 316 and a second protrusion 328 for engaging the longitudinal groove 318. An angled surface 325 of the first protrusion 326 may be formed substantially parallel to the angle of ramped surfaces 317 of each of the abutting structures 316 to minimize resistance to the proximal sliding of the abutting structures 316 over the protrusion 326. As with the prior embodiments, contact between an abutting surface 327 of the protrusion 326 and an abutting surface 319 of any of the abutting structures 316 prevents the implant 302 from moving medially beyond an initially set medial-most position. The second protrusion 328 is sized and shaped to be received within the longitudinal groove 318 such that the longitudinal groove 318 may slide therealong. The first and the second protrusions 326, 328 may be positioned on opposite sides of one another relative to the longitudinal axis of the implant 302 such that engagement of the first protrusion 326 with the plurality of notches 316 and engagement of the second protrusion 328 with the longitudinal groove 318 prevents rotation of the shaft 312 of the implant 302 about a longitudinal axis of the opening 308. The proximal end 380 of the second element 320 may also include a groove 338 surrounding the opening 384 for receiving a distal end 342 of the biasing member 340 so that the biasing member 340 urges the second element 320 into contact with the implant 302.

The second element 320 further includes a longitudinal element 388 extending from the outer surface 386 along at least a portion of a length of the second element 320. As shown in FIG. 27, the longitudinal element 388 may be configured to be slidable within a longitudinal slot 390 within the channel 310 of the intramedullary nail 304 such that the second element 320 and the intramedullary nail 304 are movable relative to one another along the longitudinal axis, but incapable of rotating relative to one another about the longitudinal axis.

The implant 302 may be inserted into the oblique opening 308 of the intramedullary nail 304 until the implant 302 is in a desired position relative to the nail 304 and the bone. Once a desired position had been reached, the assembled locking mechanism 306 may be inserted into the channel 310 of the intramedullary nail 304 by aligning the longitudinal element 388 with the longitudinal slot 390 such that the locking mechanism 306 may be slid longitudinally through the nail 304. The driving tool may then be inserted into the driving means 376 to drive the locking mechanism 306 a desired distance into the channel 310 by rotating the first element 318 relative to the second element 320 as would be understood by those skilled in the art. Thus, the channel 310 may include a threading (not shown) corresponding to the threading 366 of the first element 318 such that the first element 318 and the channel 310 may engage one another. As the first element 318 rotates about the longitudinal axis, the first element 318 pushes the second element 320 further into the channel 310. The locking mechanism 306 may be driven into the channel 310 until the distal end 382 of the second element 320 contacts the shaft 312 of the implant 302.

The implant 302 should be positioned such that upon contact of the locking mechanism 306 with the shaft 312, the first protrusion 326 engages one of the abutting structures 316 corresponding to the desired medial-most position of the implant 302 and the second protrusion 328 engages the longitudinal groove 318. As with the previously described embodiments, after the implant 302 has been engaged by the locking mechanism 306, the implant 302 may move laterally relative to the opening 308 but is prevented from moving medially by contact between the abutting surface 327 of the protrusion 326 and the abutting surface 319 of the corresponding abutting structure 316 of the implant with the biasing member 340 operating to maintain the required contact between the protrusion 326 and the corresponding abutting structure 316.

As shown in FIGS. 28-34, a device 400 according to a further embodiment of the invention may be substantially similar to the device 300, but in addition to being comprised of an implant 402 and intramedullary nail 404, a ratchet mechanism thereof comprises first and second portions 406 and 492, respectively, on opposite sides of the implant 402 from one another. As shown in FIG. 28, the implant 402 includes a shaft 412 including a plurality of abutting structures 416 distributed along a portion of a length of the shaft 412. Similarly to the implants 102, 202 and 302, each of the abutting structures 416 is angled toward a proximal end 414 of the shaft 412 with a distal facing abutting surface 419 which, in a first configuration, engages a pawl of the second portion 492 of the locking mechanism to prevent movement of the implant 402 medially after an initial position of the implant 402 is set (e.g., upon implantation) while allowing lateral migration of the implant 402.

The intramedullary nail 404 may be substantially similar to the intramedullary nail 304, except that a channel 410 extends across the oblique opening 408 from a proximal end 494 proximal of the opening 408 to a distal end 496 distal of the oblique opening 408. The first portion 406 of the locking mechanism is housed in the portion of the channel 410 extending proximal of the oblique opening 408 while the second portion 492 is housed in the portion of the channel 410 distal of the oblique opening 408.

Figure 30:
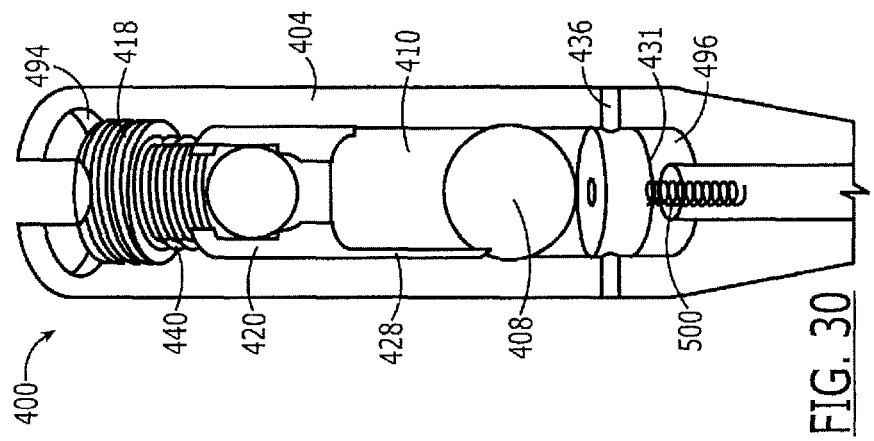
FIG. 30 shows a perspective view of the intramedullary nail, locking mechanism and the pawl of FIG. 29.
Figure 29:
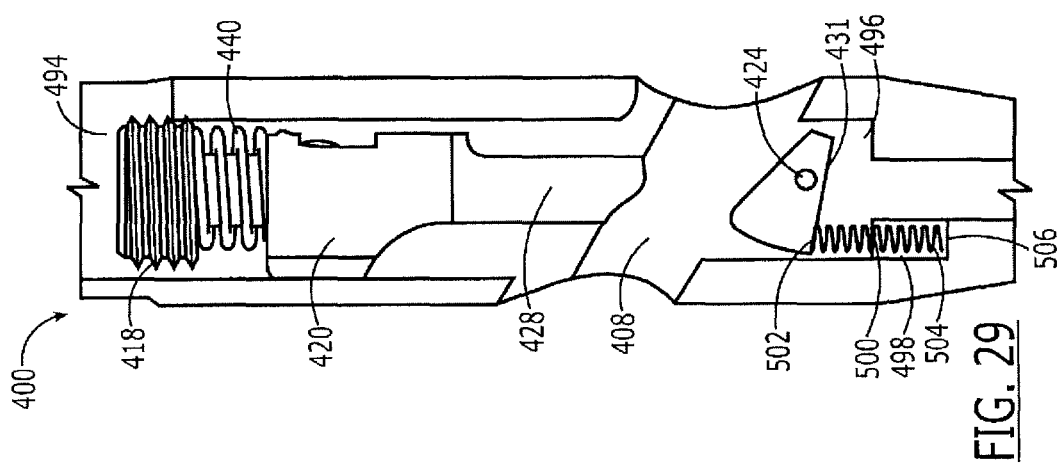
FIG. 29 shows a side view of an intramedullary nail, locking mechanism and pawl of the device of FIG. 28, in a first configuration.
Figure 32:
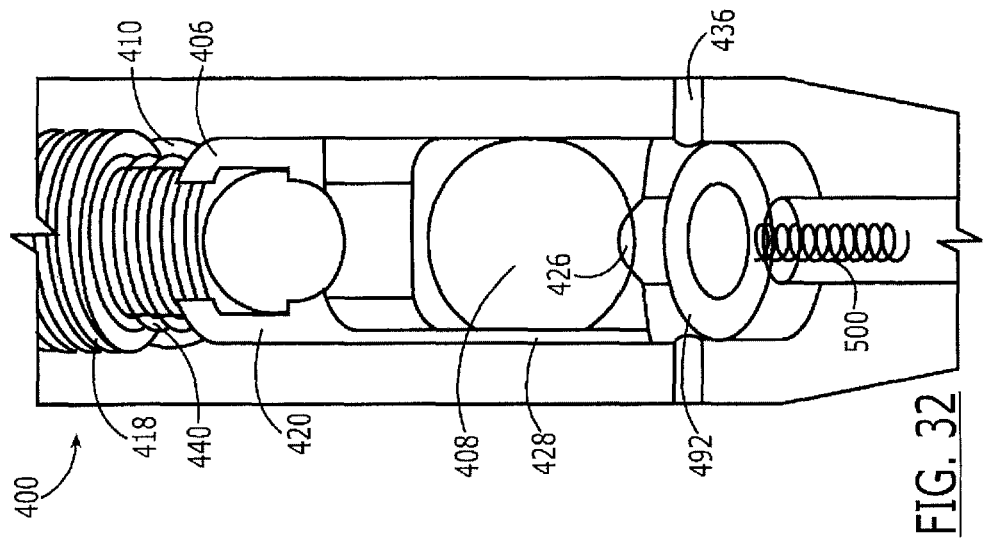
FIG. 32 shows a perspective view of the intramedullary nail, locking mechanism and the pawl of FIG. 31.
Figure 31:
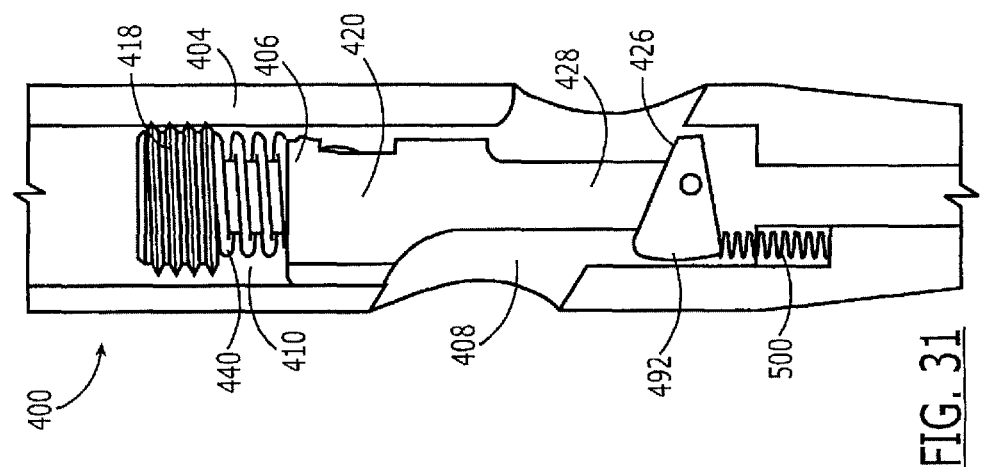
FIG. 31 shows a side view of the intramedullary nail, locking mechanism and the pawl of the device of FIG. 28, in a second configuration.
Figure 33:
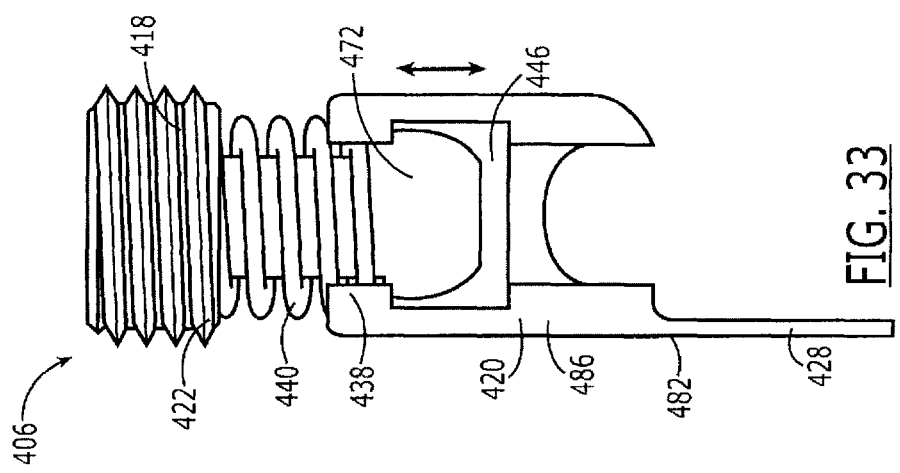
FIG. 33 shows a front view of the locking mechanism of the device of FIG. 28.

Similarly to the locking mechanism 306, the first portion 406 includes a first element 418 couplable to a second element 420 with a biasing member 440 held therebetween in a groove 422 of the first element 418 and a groove 438 of the second element. The first element 418 and the second element 420 may be coupled to one another via ball 472 of the first element 418 which is insertable into a space 446 of the second element 420, as shown in FIG. 33. The second element 420, however, includes an elongated protrusion 428 extending from a distal end 482 of an outer surface 486 of the second element 420 radially outside a circumference of the opening 408. The elongated protrusion 428 is longer than a diameter of the oblique opening 408 such that, when the locking mechanism 306 is moved longitudinally through the channel 410 from a first configuration to a second configuration, the elongated protrusion 428 crosses the opening 408 to operate the second portion 492 of the locking mechanism causing the second portion 492 to pivot. Specifically, the distal end 482 remains proximal to the opening 408 at all times while the protrusion 428 extends along and outside the opening 408 to reach the second portion 492. In the first configuration, as shown in FIGS. 29-30, the first portion 406 of the locking mechanism is positioned within the channel 410 with the elongated protrusion 428 separated from the second portion 492. As shown in FIGS. 31 and 32, when moved into the second configuration, the first portion 406 of the locking mechanism moves distally though the channel 410 moving the elongated protrusion 428 distally past the oblique opening 408 to pivot the second portion 492 so that a pawl 426 protruding from an implant facing surface 430 of the second portion 492 engages the abutting structure 416 corresponding to the desired medial-most position of the implant 402.

Figure 34:
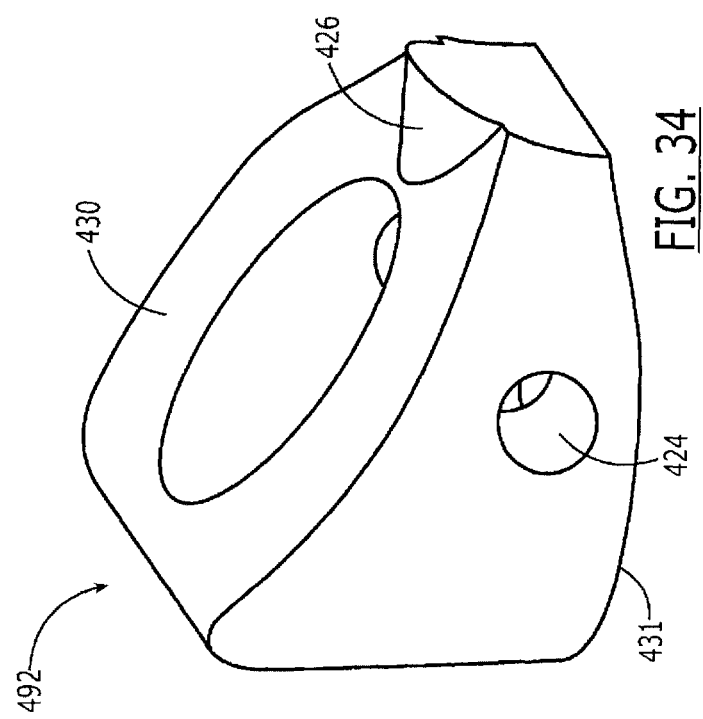
FIG. 34 shows a perspective view of a pawl of the device of FIG. 28.

As shown in FIG. 34, the second portion 492 is sized and shaped to fit within the portion of the channel 410 extending distally of the opening 408. A proximal surface 430 thereof may be angled to substantially align with a surface of the oblique opening 408 when in the first configuration. The second portion 492 is rotatably mounted in the channel 410 including, for example, a hole 424 for receiving a pin (not shown) inserted via a corresponding hole 436 in the intramedullary nail 404. The second portion 492 rotates about the pin when contacted by the protrusion 428 so that the pawl 426 pivots into the opening 408 to engage the abutting structures of the implant 402. To bias the second portion 492 toward the first configuration in which the pawl 426 remains outside the oblique opening 408, the device 400 further comprises a biasing member lumen 498 within the intramedullary nail 405 and a biasing member 500. The biasing member 500 may be housed within the lumen 498 such that a proximal end 502 of the biasing member 500 abuts the distal end 431 of the second portion 492 while a distal end 504 of the biasing member 500 abuts a distal end 506 of the lumen 498. Thus, the second portion 492 is biased toward the first configuration at all times except when the elongated protrusion 428 presses the implant facing surface 430 of the second portion 492 to the second configuration.

The device 400 may be used in substantially the same manner as the devices 100, 200 and 300. Upon positioning of the intramedullary nail 404 within the femoral shaft, the implant 402 may be inserted through the oblique opening 408 of the intramedullary nail while the first and second portions 406, 492, respectively, of the locking mechanism are in the first configuration—i.e., with neither the elongated protrusion 428 nor the pawl 426 extending into the opening 408. After the implant 402 has been inserted through the opening 408 to a desired position in the bone, the first portion 406 is moved into the second configuration in the same manner described above for the device 300 to move the elongated protrusion 428 distally until it presses against the implant facing surface 430 of the second portion 492, pivoting the second portion 492 and moving the pawl 426 into the oblique opening 408 to engage the abutting structure 416 corresponding to the desired position of the implant 402 and defining a medial-most position for the implant 402. As described above, the geometry of the abutting structures 416 is selected to permit lateral migration of the implant 402 through the opening 408.

As shown in FIGS. 35-41, a device 600 according to yet another embodiment of the invention may be substantially similar to the device 300 except as specifically described below. As shown in FIG. 35, the device 600 comprises an implant 602, an intramedullary nail 604 and a locking mechanism 606. As shown in FIG. 36, the implant 602 includes a shaft 612 with a single recessed and tapered surface 616 as opposed to the plurality of abutting surfaces as described above in regard to implant 302. The tapered surface 616 extends from a proximal end 614 to a distal end 615 with a taper of the surface 618 increasing from the proximal end 614 to the distal end 615 so that a length of a wall 614' at the proximal end 614 is less than a length of a wall 615' at the distal end 615. The tapered surface 616 is adapted and configured to receive a portion of the lock mechanism 606. The intramedullary nail 604 may be substantially similar to the intramedullary nail 304, including an oblique opening 608 for receiving the implant 602 and a channel 310 for housing the locking mechanism 606 therein, proximally of the oblique opening 608 toward a proximal end of the intramedullary nail 604.

Figure 38:
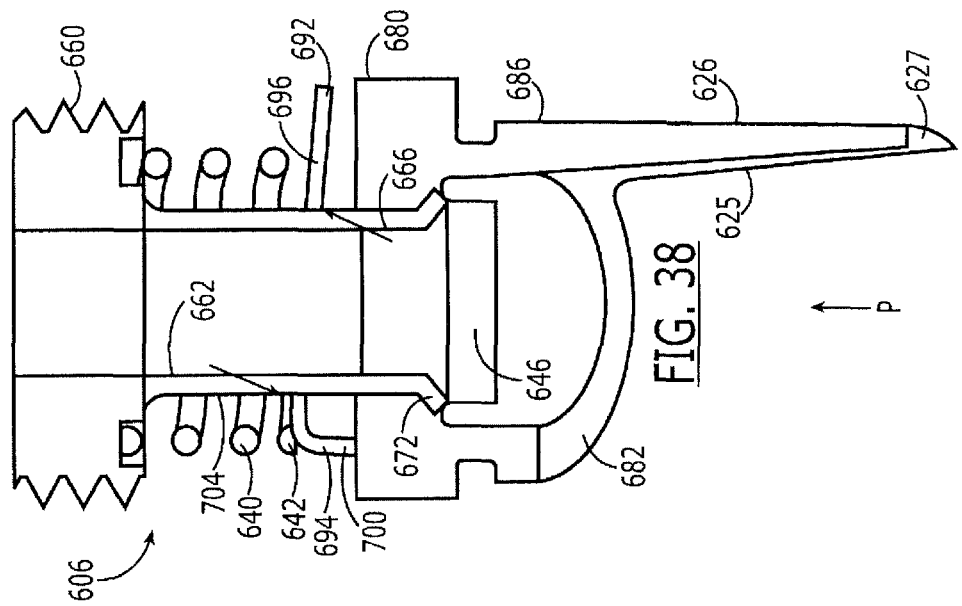
FIG. 38 shows a cross-sectional side view of the locking mechanism of FIG. 37.
Figure 37:
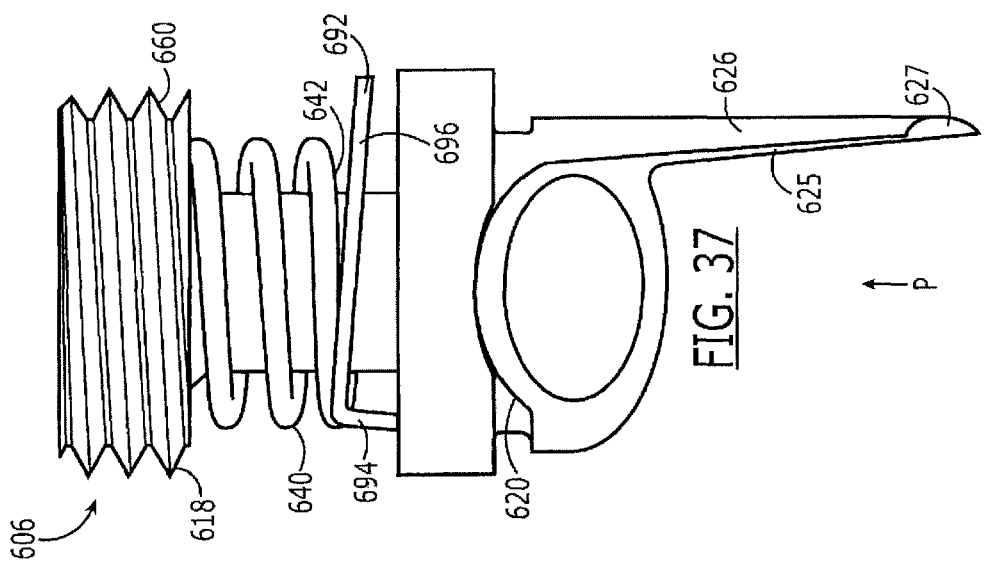
FIG. 37 shows a side view of a locking mechanism of the device of FIG. 35.

As shown in FIGS. 37-38, the locking mechanism 606 may be substantially similar to the locking mechanism 306 of the device 300. Similarly, the lock mechanism 606 includes a first element 618 couplable to a second element 620 with a biasing member 640 (e.g., a spring) held therebetween. In addition to the biasing member 640, the lock mechanism 606 further includes a canted plate 692 held between a distal end 642 of the of the biasing member 640 and a proximal end 680 of the second element 620 selectively preventing movement of the second element 620 toward the first element 618. Specifically, the canted plate 692 includes an opening 698 therethrough closely matching in size and shape an outer surface of a shaft 662 of the first element 618 so that, when the canted plate 692 is angled away from a plane substantially perpendicular to a longitudinal axis of the shaft 662, frictional engagement between a perimeter of the opening 698 and the outer surface of the shaft 6662 prevents relative movement between the first element 618 and the second element 620. The first element 618 is substantially similar to the first element 318, including a head portion 660 at a proximal end of the shaft 662 and a coupling element 672 at a distal end 666 thereof configured to engage a correspondingly shaped recess in the second element 620. A threading of the head portion 660 may engage an inner surface of the intramedullary nail 604 in the same manner described above.

The second element 620 may be substantially similar to the second element 320, extending from a proximal end 680 to a distal end 682 and including a space 646 in a central portion thereof for slidably accommodating the coupling element 672 of the first element 618 to permit relative movement therebetween along a longitudinal axis of the intramedullary nail 604. In place of the first and second protrusions of the previous embodiments, the second element 620 includes a single elongate protrusion 626 engaging the tapered surface 616 of the implant 602. The elongate protrusion 626 extends from the distal end 682 of an outer surface 686 of the second element 620 and tapers to a reduced thickness toward a distal tip 626 thereof. A taper of the elongate protrusion 626 may be selected so that the thin distal tip 626 may be received within the thinner distal end 615 of the tapered surface 616 with the increasing depth of the tapered surface 616 permitting the progressively thicker more proximal portions of the protrusion 626 to enter into engagement with the tapered surface 616 as the implant 602 is advanced distally through the nail 604. The tapered surface 616 may be formed so that, when the implant 602 has been advanced a desired distance through the nail 604, the protrusion 626 is fully received against the tapered surface 616 adjacent to the proximal end 614 thereof locking the implant 602 in a distal-most permitted position. Specifically, as the biasing member 640 moves the second element 620 distally urging the protrusion 626 further into engagement with the tapered surface 616, the canted plate 692 acts as a locking preventing the second element 620 from being moved proximally back toward the first element 618. This maintains the thicker proximal portion of the protrusion 626 in engagement with the tapered surface 616 preventing distal movement of the implant 602 relative to the nail 604 as the thickness of the proximal portion of the protrusion 626 exceeds a depth of the more distal portion of the tapered surface 616. A length of the elongate protrusion 626 is substantially equal to or greater than a diameter of the oblique opening 608 such that an entire width of the tapered surface 616 of the implant 602 may be engaged by a contacting surface 625 of the elongate protrusion 626.

The implant 602 may be inserted through the opening 608 into a desired position within the bone. During insertion of the implant 602, the locking mechanism 606 is in a first position within the intramedullary nail 604 in which the elongate protrusion 626 does not extend into the opening 608. Once the implant 602 has been inserted through the opening 608 to the desired position, the locking mechanism 606 is driven distally through the channel 610 to a second position in which the elongate protrusion 626 contacts the implant 602 and the contacting surface 625 abuts the recessed and tapered portion 616. Thus, it will be understood by those of skill in the art that, when implanted to the desired depth within the bone, the tapered surface 616 of the implant 602 extends across the opening 608 of the intramedullary nail 604.

Figure 39:
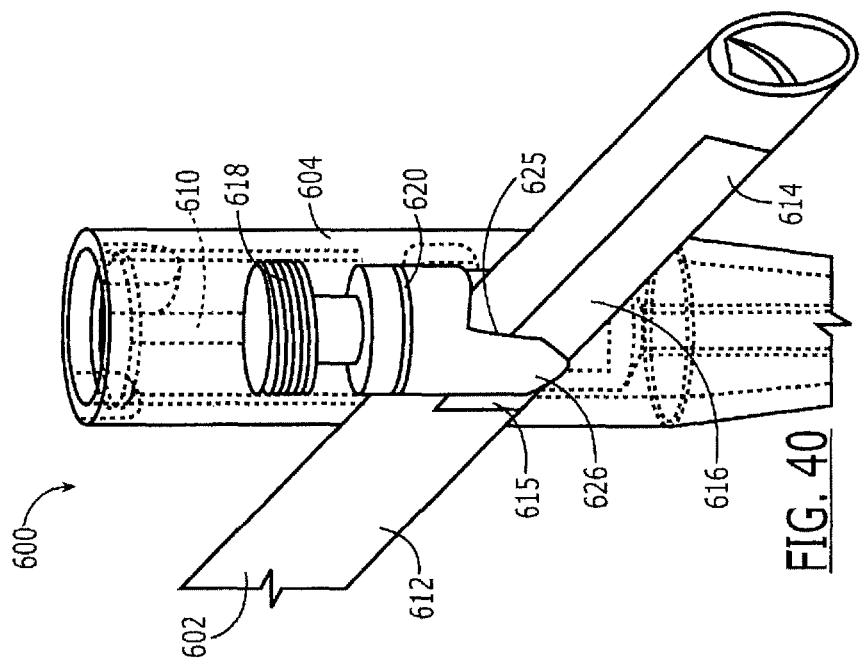
FIG. 39 shows a perspective view of the device of FIG. 35, in an initial implanted position.
Figure 40:
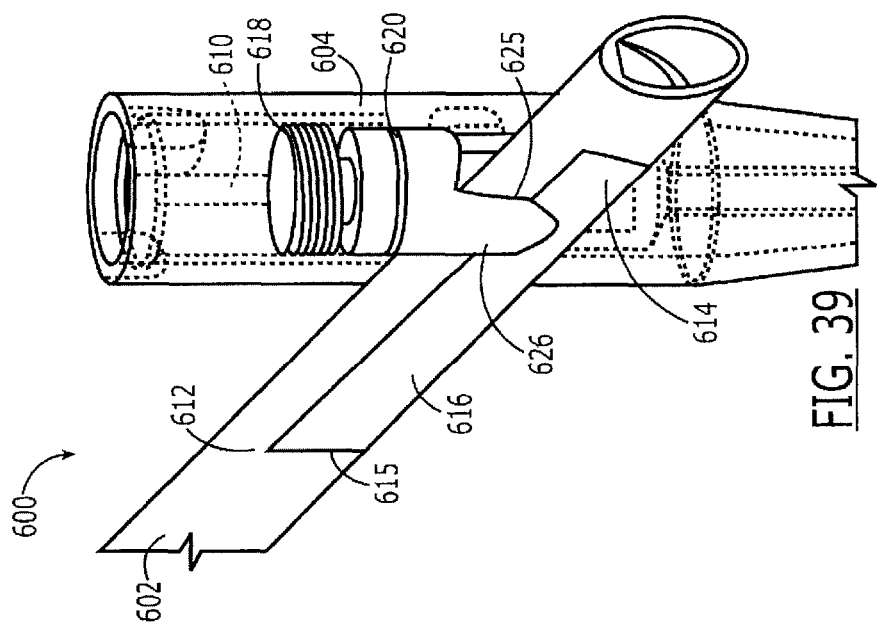
FIG. 40 shows a perspective view of the device of FIG. 35, in a final implanted position.

Specifically, with the locking mechanism 606 in the second position, the device 600 is in an initial implanted position, as shown in FIG. 39 with a distal portion of the contacting surface 625 abutting the tapered surface 616. Due to the increasing taper of the tapered surface 616 distally along the shaft 612 and the biasing member 640 which biases the second element 620 of the locking mechanism 606 to move away from the first element 618 along a longitudinal axis of the intramedullary nail 604, the implant 602 is permitted to migrate proximally through the opening 608 while maintaining contact between the contacting surface 625 and the tapered surface 616 toward a final proximal-most position, as shown in FIG. 40. The final position is reached after the implant 602 has moved laterally through the opening 608 until a width of the distal end 615 of the tapered surface 616 is contacted by the contacting surface 625. As the implant 602 moves laterally through the opening 608, the biasing member 640 pushes the second portion 620 of the locking mechanism distally such that the elongate protrusion 626 maintains constant contact with the tapered surface 616.

Figure 41:
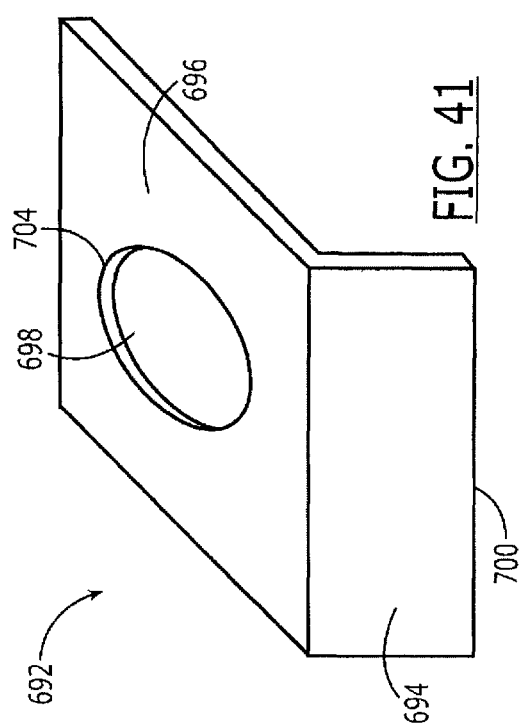
FIG. 41 shows a perspective view of a canted plate of the locking mechanism of FIG. 37.

At all times until and after the implant 602 reaches the final implanted position, the implant 602 is prevented from moving medially through the opening 608 via the canted plate 692 which locks the locking mechanism 606 preventing the second portion 620 from moving proximally within the channel 610 toward the first element 618 which is fixed within the intramedullary nail 604. As shown in FIG. 41, the canted plate 692 includes a first portion 694 and a second portion 696 angled relative to one another, substantially perpendicularly of one another. As described above, the second portion 696 includes an opening 698 extending therethrough with a proximal surface of the canted plate 692 engaging a distal end 642 of the biasing member 640 while a distal end 700 of the first portion 694 engages a proximal surface 680 of the second element 620 with the shaft 662 of the first element 618 received through the opening 696, a surface of the second portion 696 abutting the distal end 642 of the biasing member 640, while an edge 700 of the first portion 694 abuts the proximal end 680 of the second portion 620. The opening 698 is only slightly larger than a perimeter of the shaft 662 such when the implant 602 attempts to move medially through the oblique opening 608, the implant 602 pushes the second portion 620 in a direction P, angling the second portion 696 relative to the shaft 662 and bringing an inner surface 702 of the opening 698 into contact with an outer surface 704 of the shaft 662 preventing the shaft 662 from sliding therethrough and preventing the second portion 620 from moving in the direction P.

The device 600 may be used in substantially the same manner as described above in regard to the device 300. Once the intramedullary nail 604 has been positioned in an intramedullary canal of a bone, the implant 602 may be inserted medially through the oblique opening 608 until the implant 602 is in the desired position in the bone. As the implant 602 is being inserted through the opening 608, the locking mechanism 606 is maintained in the first position with the elongate protrusion 626 held proximally above the opening 608, leaving a clear path for the insertion of the implant 602 therethrough. After the implant 602 has reached a desired distal-most position in the bone with the tapered surface 616 extending across the opening 608 of the intramedullary nail 604, the locking mechanism 606 is driven distally into the intramedullary nail 604 until the elongate protrusion 626 extends into the opening 608 with the contacting surface 625 in engagement with the tapered surface 616 of the implant 602 in the second position. Even after the implant 602 is within the opening 608 in the initial implanted position, the implant 602 move proximally through the opening 608 while distal movement relative to the nail 604 is substantially prevented. However, once the implant 602 has reached the final implanted position, the implant 602 is prevented from further movement proximally and distally relative to the nail 604 as described above.

It will be apparent to those skilled in the art that various modifications and variations can be made in the structure and the methodology of the present invention, without departing from the spirit or scope of the invention. Thus, it is intended that present invention cover the modifications and variations of this invention provided that they come within the scope of the appended claims and their equivalents.

What is claimed is:

1. A device for treating fractures, comprising:
an intramedullary member sized and shaped for insertion along a longitudinal axis of a bone within a medullary canal thereof, the intramedullary member including an opening extending obliquely therethrough, the opening, when the intramedullary member is in a desired position within a bone, aligning with a desired axis along which an implant is to be inserted into a bone, the intramedullary member including a channel formed therewithin, the channel extending along a longitudinal axis of the nail and open to the opening;
an implant sized to be slidably received through the opening and inserted along the desired axis, the implant including an implant abutting structure; and
a locking mechanism mounted in the channel including a locking mechanism abutting structure extending into the opening aligned to engage the implant abutting structure permitting lateral movement of the implant relative to the intramedullary member while preventing medial movement of the implant relative to the intramedullary member,
wherein the locking mechanism abutting structure is formed as a pawl which moves relative to the intramedullary nail along the longitudinal axis between a first configuration in which the pawl disengages from the implant abutting structure and a second configuration in which the pawl engages the implant abutting structure to prevent medial movement of the implant,
wherein the locking mechanism includes a biasing member biasing the pawl toward the second configuration, and
wherein the implant further includes a longitudinal groove along a portion of a length thereof, the longitudinal groove being positioned to align with a projection of the locking mechanism when the implant is in a locked configuration wherein, when the implant is in an insertion orientation, contact between the projection and the implant moves the pawl to the first configuration.

2. The device of claim 1, wherein the projection is coupled to the pawl so that, when the implant is in the locked configuration, movement of the projection into the groove allows the pawl to move into the second configuration through the operation of the biasing member.

3. The device of claim 1, wherein the desired axis is along an axis of a femoral head and neck.

4. The device of claim 1, wherein the implant further includes a first longitudinal groove along a portion of a length thereof on a side of the implant engaging the locking mechanism abutting structure, the first groove being tapered from a maximum depth in the implant at a distal end of the first groove.

5. The device of claim 4, wherein the locking mechanism abutting structure extends to a tapered distal end, a minimum depth of the first groove receiving the tapered distal end such that thicker proximal portions of the locking mechanism abutting structure are receivable within an increasing depth of the shaft.

6. The device of claim 4, wherein the locking mechanism includes a first member, a second member including the locking mechanism abutting structure and a canted plate, the canted plate including a first portion which, when maintained in a plane substantially perpendicular to a longitudinal axis of the intramedullary member, permits the second member to move along the longitudinal axis relative to the first member and, when in a plane which is not perpendicular to the longitudinal axis of the intramedullary member frictionally engages one of the first and second members preventing the one of the first and second members from sliding through an opening formed in the first portion.

7. The device of claim 6, wherein the locking mechanism includes a biasing member biasing the locking mechanism abutting structure distally into engagement with the implant, the canted plate including a second portion extending substantially perpendicular to the first portion, a distal end of the second portion engaging a proximal portion of the locking mechanism abutting structure while a proximal side of the first portion engages a distal end of the biasing member.

8. A device for treating fractures, comprising:
an intramedullary member sized and shaped for insertion along a longitudinal axis of a bone within a medullary canal thereof, the intramedullary member including an opening extending obliquely therethrough, the opening, when the intramedullary member is in a desired position within a bone, aligning with a desired axis along which an implant is to be inserted into a bone, the intramedullary member including a channel formed therewithin, the channel extending along a longitudinal axis of the nail and open to the opening;
an implant sized to be slidably received through the opening and inserted along the desired axis, the implant including an implant abutting structure; and
a locking mechanism mounted in the channel including a locking mechanism abutting structure extending into the opening aligned to engage the implant abutting structure permitting lateral movement of the implant relative to the intramedullary member while preventing medial movement of the implant relative to the intramedullary member,
wherein the implant further includes first and second longitudinal grooves along a portion of a length thereof on opposite sides of the implant abutting structure, and
wherein the locking mechanism includes a pair of protrusions, each of the protrusions being positioned to engage a corresponding one of the first and the second longitudinal grooves to prevent rotation of the implant about a central axis of the opening.

9. The device of claim 8, wherein the intramedullary member includes a locking mechanism lumen extending through the intramedullary member to open to the channel, the locking mechanism including an actuation feature aligned with the locking mechanism lumen.

10. The device of claim 9, wherein the actuation feature comprises a ramped surface which, when engaged by an instrument inserted through the locking mechanism lumen moves the pawl to the first configuration.

11. A device for treating fractures, comprising:
an intramedullary member sized and shaped for insertion along a longitudinal axis of a bone within a medullary canal thereof, the intramedullary member including an opening extending obliquely therethrough, the opening, when the intramedullary member is in a desired position within a bone, aligning with a desired axis along which an implant is to be inserted into a bone, the intramedullary member including a channel formed therewithin, the channel extending along a longitudinal axis of the nail and open to the opening;
an implant sized to be slidably received through the opening and inserted along the desired axis, the implant including an implant abutting structure; and
a locking mechanism mounted in the channel including a locking mechanism abutting structure extending into the opening aligned to engage the implant abutting structure permitting lateral movement of the implant relative to the intramedullary member while preventing medial movement of the implant relative to the intramedullary member, wherein the locking mechanism abutting structure is formed as a pawl which moves relative to the intramedullary nail along the longitudinal axis between a first configuration in which the pawl disengages from the implant abutting structure and a second configuration in which the pawl engages the implant abutting structure to prevent medial movement of the implant, and wherein the locking mechanism includes first and second components coupled to one another for movement relative to one another along and about a longitudinal axis of the intramedullary member.

12. The device of claim 11, wherein the first component include a driving structure at a proximal end thereof and threading about an outer surface thereof engaging a corresponding threading in the channel such that rotation of the locking mechanism via the driving structure drives the pawl between the first and second configurations.

13. The device of claim 12, wherein the second component includes a longitudinal element along an outer surface thereof which aligns with a longitudinal slot within the channel preventing rotation of the second element rotate relative to the intramedullary nail.

14. A device for treating fractures, comprising:
an intramedullary member sized and shaped for insertion along a longitudinal axis of a bone within a medullary canal thereof, the intramedullary member including an opening extending obliquely therethrough, the opening, when the intramedullary member is in a desired position within a bone, aligning with a desired axis along which an implant is to be inserted into a bone, the intramedullary member including a channel formed therewithin, the channel extending along a longitudinal axis of the nail and open to the opening;
an implant sized to be slidably received through the opening and inserted along the desired axis, the implant including an implant abutting structure; and
a locking mechanism mounted in the channel including a locking mechanism abutting structure extending into the opening aligned to engage the implant abutting structure permitting lateral movement of the implant relative to the intramedullary member while preventing medial movement of the implant relative to the intramedullary member,
wherein the locking mechanism abutting structure is formed as a pawl which moves relative to the intramedullary nail along the longitudinal axis between a first configuration in which the pawl disengages from the implant abutting structure and a second configuration in which the pawl engages the implant abutting structure to prevent medial movement of the implant, and
wherein the channel includes a proximal portion extending through a portion of the intramedullary member proximal of the opening and a distal portion extending through a portion of the intramedullary member distal of the opening, the locking mechanism including a first portion in the proximal portion of the channel and a second portion in the distal portion of the channel, a protrusion extending from one of the first and second portions being movable relative to the opening to engage the other of the first and second portions, the other of the first and second portions including the pawl and moving, through contact with the protrusion to the first configuration.

15. A method comprising:
inserting an intramedullary member into a medullary canal of a bone, the intramedullary member including a channel formed therein along a longitudinal axis thereof;
inserting an implant into a bone via an opening in the intramedullary member, the opening being open to the channel, a shaft of the implant including a plurality of abutting structures distributed along a portion of a length of the shaft, each of the abutting structures including an angled lateral surface and a medially-facing abutting surface;
moving a locking mechanism mounted in the channel to a locked configuration in which a pawl of the locking mechanism extends into the opening to engage the abutting surface of one of the abutting structures corresponding to a desired medial-most position of the implant, the angled lateral surfaces of the abutting structures permitting lateral movement of the implant relative to the pawl; and
rotating a portion of the locking mechanism to drive the locking mechanism into the intramedullary member to move the pawl away from the locked configuration.

16. The method of claim 15, wherein during insertion, the shaft presses on a protrusion of the locking mechanism to move the locking mechanism away from the locked configuration so that the pawl does not engage the abutting structures.

17. The method of claim 15, further comprising engaging the locking mechanism with a pin to move the pawl away from the locked configuration.

18. The method of claim 15, wherein the pawl is urged toward the locked configuration by a biasing member.

* * * * *

UNITED STATES PATENT AND TRADEMARK OFFICE
CERTIFICATE OF CORRECTION

| | | |
|---|---|---|
| PATENT NO. | : 9,084,643 B2 | Page 1 of 1 |
| APPLICATION NO. | : 13/122887 | |
| DATED | : July 21, 2015 | |
| INVENTOR(S) | : Mikhail et al. | |

It is certified that error appears in the above-identified patent and that said Letters Patent is hereby corrected as shown below:

In the claims

Claim 12, Column 17, Line 16:

"include a driving structure at a proximal end thereof and" should read "includes a driving structure at a proximal end thereof and".

Claim 13, Column 17, Lines 23-24:

"which aligns with a longitudinal slot within the channel preventing rotation of the second element rotate relative to the" should read "which aligns with a longitudinal slot within the channel preventing rotation of the second element relative to the".

Signed and Sealed this
Fifteenth Day of December, 2015

Michelle K. Lee
*Director of the United States Patent and Trademark Office*